(12) United States Patent
Byrd

(10) Patent No.: US 8,052,607 B2
(45) Date of Patent: Nov. 8, 2011

(54) ULTRASOUND IMAGING CATHETER WITH PIVOTING HEAD

(75) Inventor: Charles Bryan Byrd, Medford, NJ (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 745 days.

(21) Appl. No.: 12/107,759

(22) Filed: Apr. 22, 2008

(65) Prior Publication Data

US 2009/0264759 A1 Oct. 22, 2009

(51) Int. Cl.
*A61B 8/14* (2006.01)

(52) U.S. Cl. .................. 600/459; 600/437; 600/462

(58) Field of Classification Search ............ 600/437–467
See application file for complete search history.

(56) References Cited

U.S. PATENT DOCUMENTS

| | | |
|---|---|---|
| 4,161,121 A | 7/1979 | Zitelli et al. |
| 4,241,610 A | 12/1980 | Anderson |
| 4,462,408 A | 7/1984 | Silverstein et al. |
| 4,519,260 A | 5/1985 | Fu et al. |
| 4,576,177 A | 3/1986 | Webster, Jr. |
| 4,605,009 A | 8/1986 | Pourcelot et al. |
| 4,841,977 A | 6/1989 | Griffith et al. |
| 4,890,268 A | 12/1989 | Smith et al. |
| 4,917,097 A | 4/1990 | Proudian et al. |
| 4,951,677 A | 8/1990 | Crowley et al. |
| 5,002,059 A | 3/1991 | Crowley et al. |
| 5,090,956 A | 2/1992 | McCoy |
| 5,105,819 A | 4/1992 | Wollschlager et al. |
| 5,158,087 A | 10/1992 | Suzuki et al. |
| 5,170,793 A | 12/1992 | Takano et al. |
| 5,195,968 A | 3/1993 | Lundquist et al. |
| 5,254,088 A | 10/1993 | Lundquist et al. |
| 5,279,559 A | 1/1994 | Barr |
| 5,307,816 A | 5/1994 | Hashimoto et al. |

(Continued)

FOREIGN PATENT DOCUMENTS

EP 0039045 11/1981

(Continued)

OTHER PUBLICATIONS

Keith S. Dickerson et al., "Comparison of Conventional and Transverse Doppler Sonograms", J. Ultrasound Med., 1993, pp. 497-506, vol. 12.

(Continued)

*Primary Examiner* — Sanjay Cattungal
(74) *Attorney, Agent, or Firm* — The Marbury Law Group, LLC

(57) ABSTRACT

An ultrasound imaging catheter system includes a pivot head assembly coupled between a ultrasound transducer array and the distal end of the catheter. The pivot head assembly includes a pivot joint enabling the transducer array to pivot through a large angle about the catheter centerline in response pivot cables controlled by a wheel within a handle assembly. Pivoting the ultrasound transducer array approximately 90° once the catheter is positioned by rotating the catheter shaft and bending the distal section of the catheter, clinicians may obtain orthogonal 2-D ultrasound images of anatomical structures of interest in 3-D space. Combining bending of the catheter by steering controls with pivoting of the transducer head enables a greater range of viewing perspectives. The pivot head assembly enables the transducer array to pan through a large angle to image of a larger volume than possible with conventional ultrasound imaging catheter systems.

20 Claims, 17 Drawing Sheets

U.S. PATENT DOCUMENTS

| | | | |
|---|---|---|---|
| 5,309,914 A | 5/1994 | Iinuma | |
| 5,325,860 A | 7/1994 | Seward et al. | |
| 5,336,182 A | 8/1994 | Lundquist et al. | |
| 5,345,938 A | 9/1994 | Nishiki et al. | |
| 5,345,940 A | 9/1994 | Seward et al. | |
| 5,351,692 A * | 10/1994 | Dow et al. | 600/463 |
| 5,357,550 A | 10/1994 | Asahina et al. | |
| 5,358,478 A | 10/1994 | Thompson et al. | |
| 5,364,351 A | 11/1994 | Heinzelman et al. | |
| 5,372,138 A | 12/1994 | Crowley et al. | |
| 5,385,148 A | 1/1995 | Lesh et al. | |
| 5,395,327 A | 3/1995 | Lundquist et al. | |
| 5,438,997 A | 8/1995 | Sieben et al. | |
| 5,456,258 A | 10/1995 | Kondo et al. | |
| 5,456,664 A | 10/1995 | Heinzelman et al. | |
| 5,470,350 A | 11/1995 | Buchholtz et al. | |
| 5,499,630 A | 3/1996 | Hiki et al. | |
| 5,515,853 A | 5/1996 | Smith et al. | |
| 5,515,856 A | 5/1996 | Olstad et al. | |
| 5,531,686 A | 7/1996 | Lundquist et al. | |
| 5,560,362 A | 10/1996 | Sliwa, Jr. et al. | |
| 5,588,432 A | 12/1996 | Crowley | |
| 5,601,601 A | 2/1997 | Tal et al. | |
| 5,622,174 A | 4/1997 | Yamazaki | |
| 5,662,116 A | 9/1997 | Kondo et al. | |
| 5,697,965 A | 12/1997 | Griffin, III | |
| 5,699,805 A | 12/1997 | Seward et al. | |
| 5,701,897 A | 12/1997 | Sano | |
| 5,704,361 A | 1/1998 | Seward et al. | |
| 5,713,363 A | 2/1998 | Seward et al. | |
| 5,715,817 A | 2/1998 | Stevens-Wright et al. | |
| 5,722,403 A | 3/1998 | McGee et al. | |
| 5,749,364 A | 5/1998 | Sliwa, Jr. et al. | |
| 5,788,636 A | 8/1998 | Curley | |
| 5,795,299 A | 8/1998 | Eaton et al. | |
| 5,797,848 A | 8/1998 | Marian et al. | |
| 5,800,356 A | 9/1998 | Criton et al. | |
| 5,807,324 A | 9/1998 | Griffin, III | |
| 5,846,205 A | 12/1998 | Curley et al. | |
| 5,888,577 A | 3/1999 | Griffin, III et al. | |
| 5,891,088 A | 4/1999 | Thompson et al. | |
| 5,906,579 A | 5/1999 | Vander Salm et al. | |
| 5,916,168 A | 6/1999 | Pedersen et al. | |
| 5,921,978 A | 7/1999 | Thompson et al. | |
| 5,928,276 A | 7/1999 | Griffin, III et al. | |
| 5,931,863 A | 8/1999 | Griffin, III et al. | |
| 5,935,102 A | 8/1999 | Bowden et al. | |
| 5,938,616 A | 8/1999 | Eaton et al. | |
| 5,954,654 A | 9/1999 | Eaton et al. | |
| 6,013,072 A | 1/2000 | Winston et al. | |
| 6,033,378 A | 3/2000 | Lundquist et al. | |
| 6,039,693 A | 3/2000 | Seward et al. | |
| 6,085,117 A | 7/2000 | Griffin, III et al. | |
| 6,144,870 A | 11/2000 | Griffin, III | |
| 6,171,248 B1 | 1/2001 | Hossack et al. | |
| 6,173,205 B1 | 1/2001 | Griffin, III et al. | |
| 6,190,353 B1 | 2/2001 | Makower et al. | |
| 6,210,333 B1 | 4/2001 | Gardner et al. | |
| 6,224,556 B1 | 5/2001 | Schwartz et al. | |
| 6,228,028 B1 | 5/2001 | Klein et al. | |
| 6,228,032 B1 | 5/2001 | Eaton et al. | |
| 6,261,246 B1 | 7/2001 | Pantages et al. | |
| 6,293,943 B1 | 9/2001 | Panescu et al. | |
| 6,306,096 B1 | 10/2001 | Seward et al. | |
| 6,306,097 B1 | 10/2001 | Park et al. | |
| 6,310,828 B1 | 10/2001 | Mumm et al. | |
| 6,360,027 B1 | 3/2002 | Hossack et al. | |
| 6,368,275 B1 | 4/2002 | Sliwa et al. | |
| 6,385,489 B1 | 5/2002 | Griffin, III et al. | |
| 6,398,731 B1 | 6/2002 | Mumm et al. | |
| 6,423,002 B1 | 7/2002 | Hossack | |
| 6,440,488 B2 | 8/2002 | Griffin, III et al. | |
| 6,443,894 B1 | 9/2002 | Sumanaweera et al. | |
| 6,475,148 B1 | 11/2002 | Jackson et al. | |
| 6,475,149 B1 | 11/2002 | Sumanaweera | |
| 6,482,161 B1 | 11/2002 | Sumanaweera et al. | |
| 6,485,455 B1 | 11/2002 | Thompson et al. | |
| 6,491,633 B1 | 12/2002 | Krishnan et al. | |
| 6,503,202 B1 | 1/2003 | Hossack et al. | |
| 6,517,488 B1 | 2/2003 | Hossack | |
| 6,527,717 B1 | 3/2003 | Jackson et al. | |
| 6,532,378 B2 | 3/2003 | Saksena et al. | |
| 6,554,770 B1 | 4/2003 | Sumanaweera et al. | |
| 6,589,182 B1 | 7/2003 | Loftman et al. | |
| 6,605,043 B1 | 8/2003 | Dreschel et al. | |
| 6,607,488 B1 | 8/2003 | Jackson et al. | |
| 6,607,528 B1 | 8/2003 | Quick et al. | |
| 6,612,992 B1 | 9/2003 | Hossack et al. | |
| 6,645,147 B1 | 11/2003 | Jackson et al. | |
| 6,648,875 B2 | 11/2003 | Simpson et al. | |
| 6,709,396 B2 | 3/2004 | Flesch et al. | |
| 6,908,434 B1 | 6/2005 | Jenkins et al. | |
| 6,923,768 B2 | 8/2005 | Camus et al. | |
| 7,029,467 B2 | 4/2006 | Currier et al. | |
| 7,507,205 B2 * | 3/2009 | Borovsky et al. | 600/466 |
| 2003/0045796 A1 | 3/2003 | Friedman | |
| 2003/0158483 A1 | 8/2003 | Jackson et al. | |
| 2004/0097805 A1 | 5/2004 | Verard et al. | |
| 2004/0249282 A1 | 12/2004 | Olslad | |
| 2004/0254442 A1 | 12/2004 | Williams et al. | |
| 2005/0203390 A1 | 9/2005 | Torp et al. | |
| 2005/0228290 A1 * | 10/2005 | Borovsky et al. | 600/466 |

FOREIGN PATENT DOCUMENTS

| | | |
|---|---|---|
| WO | 2005099584 A3 | 10/2005 |

OTHER PUBLICATIONS

David J. Sahn, "Phased Arrays for Multiplane Esophageal Echos in Infants", Summary Statement, Diagnostic Radiology Study Section, Jun. 1990.

David J. Sahn, "Instrumentation and Physical Factors Related to Visualization of Stenotic and Regurgitant Jets by Doppler Color Flow Mapping", JACC, Nov. 1988, pp. 1354-1365, vol. 12, No. 5.

David J. Sahn, "Advances in Ultrasound Imaging for Congenital Heart Disease Diagnosis and Management", Pediatric Cardiology, Nov. 26-Dec. 1, 1989, Proceedings of the III World Congress of Pediatric Cardiology, Bangkok.

David J. Sahn et al., "Important Rolesof Transeophageal Color Doppler Flow Mapping Studies(TEE) in Infants with Congenital Heart Disease", Supplement to Journal of the American College of Cardiology, Feb. 1990, vol. 15, No. 2 (Supplement A).

David J. Sahn, "Applications of Color Flow Mapping in Pediatric Cardiology", Cardiology Clinics, May 1989, pp. 255-264, vol. 7, No. 2.

David J. Sahn et al., "Miniaturized High Frequency Phased Array Devices for High Resolution Neonatal and Intraoperative Imaging", Supplement to Journal of the American College of Cardiology, Feb. 1990, vol. 15, No. 2 (Supplement A).

Piero Tortoli et al., "Velocity Magnitude Estimation with Linear Arrays Using Doppler Bandwidth", Ultrasounics, 2001, pp. 157-161, vol. 39.

Lilliam M. Valdes-Cruz et al., "Transvascular Intracardiac Applications of a Miniaturized Phase-Array Ultrasonic Endoscope", Brief Rapid Communication, Mar. 1991, pp. 1023-1027, vol. 83, No. 3.

Lilliam M. Valdes-Cruz et al., "Experimental Animal Investigations of the Potential for New Approaches to Diagnostic Cardiac Imaging in Infants and Small Premature Infants from Intracardiac and Trasesophageal Approaches Using a 20MHz Real Time Ultrasound Imaging Catheter", Supplement to Journal of the American College of Cardiology, Feb. 1989, vol. 13, No. 2 (Supplement A).

P.N.T. Wells, "Velocity, Absorption and Attenuation in Biological Materials", Biomedical Ultrasonics, 1977, pp. 110-144.

Antonio L. Bartorelli, M.D. et al., "Plaque Characterization of Atherosclerotic Coronary Arteries by Intravascular Ultrasound", Echocardiography: A Journal of CV Ultrasound & Allied Tech, 1990, pp. 389-395, vol. 7, No. 4.

N. Bom et al., "Early and recent intraluminal ultrasound devices", International Journal of Cardiac Imaging, 1989, pp. 79-88, vol. 4.

R.J. Crowley et al., "Optimized ultrasound imaging catheters for use in the vascular system", International Journal of Cardiac Imaging, 1989, pp. 145-151, vol. 4.

R.J. Crowley, et al., "Ultrasound guided therapeutic catheters: recent developments and clinical results", International Journal of Cardiac Imaging, 1991, pp. 145-156, vol. 6.

Richard A. Carleton, M.D., et al., "Measurement of Left Ventricular Diameter in the Dog by Cardiac Catheterization", Circulation Research, May 1968, pp. 545-558, vol. XXII.

Taher Elkadi et al., "Importance of Color Flow Doppler (CFD) Imaging of the Right Ventricular Outflow Tract and Pulmonary Arteries by Transesophageal Echocardiography (TEE) During Surgery for CHD", Supplement III Circulation, Oct. 1990, p. III-438, vol. 82, No. 4.

Philip C. Currie, "Transeosphageal Echocardiography New Window to the Hearth", Circulation, Jul. 1989, pp. 215-217, vol. 88, No. 1.

Steven Schwartz et al., "In Vivo Intracardiac 2-D Echocardiography: Effects of Transducer Frequency, Imaging Approached and Comparison with Fiberoptic Angioscopy", JACC, Feb. 1990, pp. 29A, vol. 15, No. 2.

J. Souquet et al., "Transesophageal Phased Array for Imaging the Heart", IEEE Transactions on Biomedical Engineering, Oct. 1982, pp. 707-712, vol. BME-29, No. 10.

Craig J. Hartley, "Review of Intracoronary Doppler catheters", International Journal of Cardiac Imaging, 1989, pp. 159-168, vol. 4.

John McB. Hodgson et al., "Percutaneous Intravascular Ultrasound Imaging: Validation of a Real-Time Synthetic Aperture Array Catheter", American Journal of Cardiac Imaging, Mar. 1991, pp. 56-71, vol. 5, No. 1.

J. McB. Hodgson et al., "Clinical percutaneous imaging of corconary anatomy using an over-the-wire ultrasound catheter system", International Journal of Cardiact Imaging, 1989, pp. 187-193, vol. 4.

Brenda S. Kusay et al., "Realtime in Vivo Intracardiac Two-Dimensional Echocardiography and Color Flow Imaging: Approaches, Imaging Planes, and Echo Anatomy", Abstracts of the 62nd Scientific Sessions, 1989, p. II-581.

Charles T. Lancee, "A Transesophageal Phased Array Transducer for Ultrasonic Imaging of the Heart", 1987.

Natesa Pandian et al., "Enhanced Depth of Field in Intracardiac 2-D Echocardiography with a New Prototype, Low Frequency (12 MHz, 9 French) Ultrasound Catheter", Supplemental III Circulation, Oct. 1990, p. III-442, vol. 82, No. 4.

Natesa G. Pandian, M.D. et al., "Intravascular and Intracardiac Ultrasound Imaging: Current Research and Future Directions", Echocardiography: A Journal of CV Ultrasound & Allied Tech., 1990, pp. 377-387, vol. 7, No. 4.

Natesa G. Pandian, M.D. et al., "Intracardiac, Intravascular, Two-Dimensional, High-Frequency Ultrasound Imaging of Pulmonary Artery and Its Branches in Humans and Animals", Circulation, Jun. 1990, pp. 2007-2012, vol. 81, No. 6.

F. Ricou et al., "Applications of intravascular scanning and transesophageal echocardiography in congenital heart disease: tradeoffs and the merging of technologies", International Journal of Cardiac Imaging, 1991, pp. 221-230, vol. 6.

Samuel B. Ritter, M.D., et al., "Transesophageal real time Doppler flow imaging in congenital heart disease: experience with a new pediatric trasducer probe", 1989, Dynamedia, Inc.

Samuel B. Ritter, M.D., et al., "Pediatric Transesophageal Color Flow Imaging: Smaller Probes for Smaller Hearts", 1989.

David J. Sahn, M.D., et al., "Important Roles of Transesophageal Color Doppler Flow Mapping Studies (TEE) in Infants With Congenital Heart Disease", IACC, Feb. 1990, p. 204A, vol. 15, No. 2.

David J. Sahn, M.D. et al., "Miniaturized High Frequency Phased Array Devices for High Resolution Neonatal and Intraoperative Imaging", JACC, Feb. 1990, p. 10A, vol. 15, No. 2.

David J. Sahn, M.D., et al., "Phased Arrays for Multiplane Esophageal Echos in Infants", Grant Application, Department of Health and Human Services Public Health Service, 1992.

Steven Schwartz, M.D., et al., "Intracardiac Echocardioraphic Guidance and Monitoring During Aortic and Mitral Balloon Valvuloplasty", JACC, Feb. 1990, p. 104A, vol. 15, No. 2.

James B. Seward, M.D. et al., "Biplanar Transesophageal Echocardiography: Anatomic Correlations, Image Orientation, and Clinical Applications", Mayo Clin Proc., 1990, pp. 1198-1213, vol. 65.

James B. Seward, M.D. et al., "Wide-Field Transesophageal Echocardiographic Tomography: Feasibility Study", Mayo Clin Proc. 1990, pp. 31-37, vol. 65.

Khalid H. Sheikh, M.D., et al., "Interventional Applications of Intravascular Ultrasound Imaging: Initial Experience and Future Perspectives", Echocadiography: A Journal of CV Ultrasound & Allied Tech., pp. 433-441, vol. 7, No. 4.

Paul G. Yock, M.D., et al., "Two-Dimensional Intravascular Ultrasound: Technical Development and Initial Clinical Experience", Journal of American Society of Echocardiography, 1989, pp. 296-304, vol. 2, No. 4.

Paul G. Yock, M.D. et al., "Real-Time, Two-Dimensional Catheter Ultrasound: A New Technique for High-Resolution Intravascular Imaging", JACC, Feb. 1988, p. 130A, vol. 11, No. 2.

P. Yock et al., "Intravascular Two-Dimensional Catheter Ultrasound: Initial Clinical Studies", Abstracts of the 61st Scientist Sessions, p. II-21.

Michael J. Eberle et al., "Validation of a New Real Time Percotaneous Intravascular Ultrasound Imaging Catheter", Abstracts of the 61st Scientist Sessions, p. II-21.

Natasa Pandian et al., "Intralurolonal Ultrasound Angloscopic Detection of Arterial Dissection and Intimal Flaps: In Vitro and In Vivo Studies", Abstracts of the 61st Scientist Sessions, p. II-21.

John A. Mallery et al., "Evaluation of an Intravascular ultrasound Imaging Catheter in Porcine Peripheral and Coronary Arteries In Vivo", Abstracts of the 61st Scientist Sessions, p. II-21.

Andrew Wintraub, M.D., "Realtime Intracardiac Two-Dimensional Echocardiography in the Catheterization Laboratory in Humans", Intravascular Imaging I, Mar. 19, 1990.

International Search Report (ISR) for PCT/US05/011545, Dec. 5, 2006.

Written Opinion of International Search Authority for PCT/US05/011545, Dec. 5, 2006.

International Preliminary Report on Patentability for PCT/US05/011545, Dec. 5, 2006.

"Supplementary European Search Report", EP 09733751 Feb. 1, 2011.

* cited by examiner

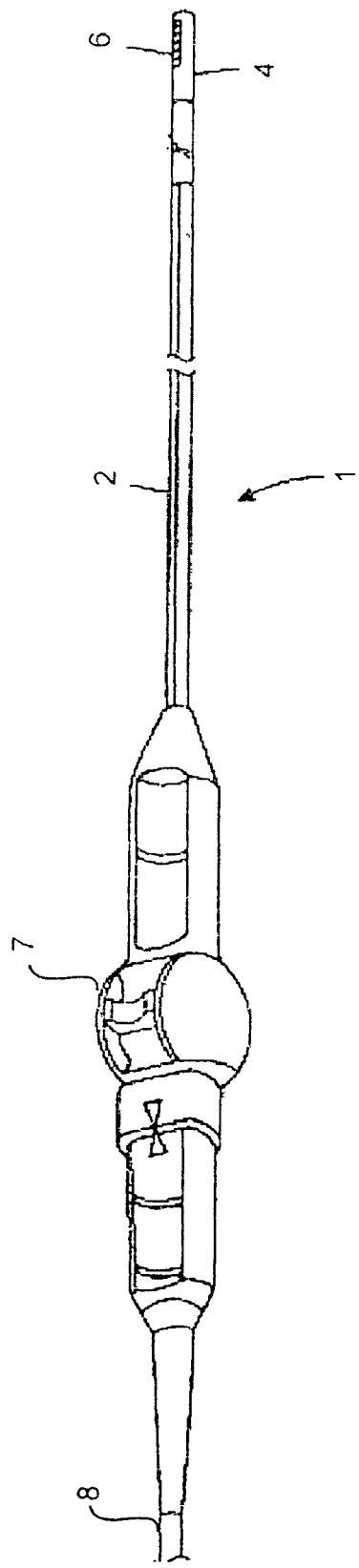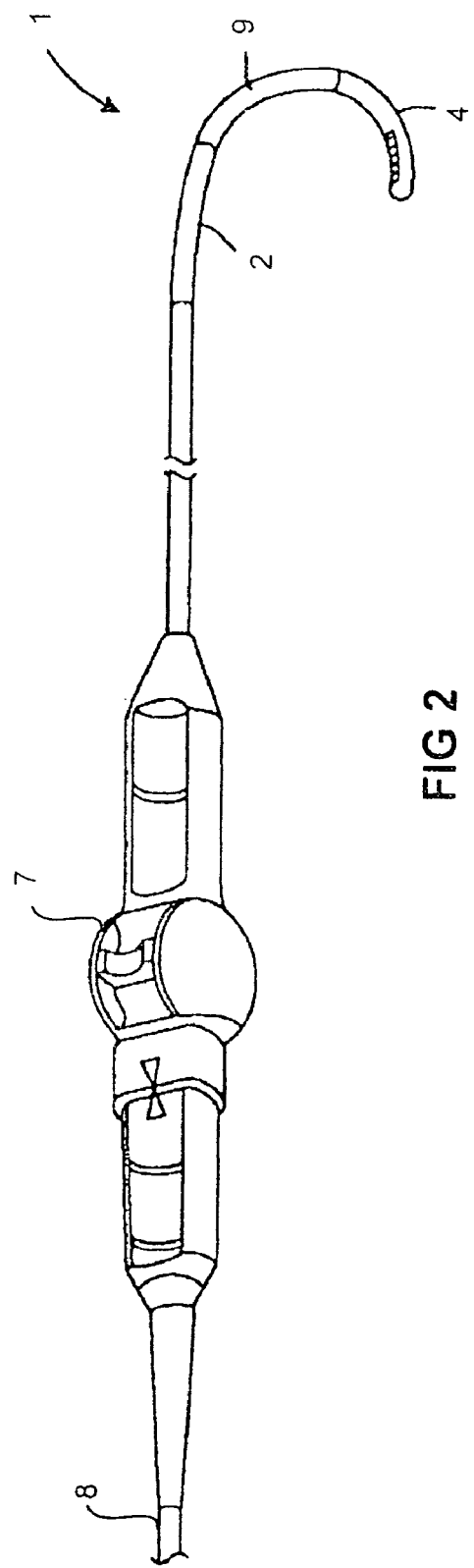
FIG 1
(Prior Art)
FIG 2
(Prior Art)

ULTRASOUND IMAGING CATHETER WITH PIVOTING HEAD

FIELD OF THE INVENTION

The present invention relates generally to catheters and more particularly to a steerable ultrasound imaging catheter with a pivoting head.

BACKGROUND

Catheters for insertion and deployment within blood vessels and cardiac chambers are well-known in the art. A variety of catheters are now utilized in the diagnosis and treatment of cardiac disease. Among the ensemble of catheters used in cardiac care are ultrasound imaging catheters which can be inserted within the heart (i.e., intracardial) to obtain two-dimensional ultrasound images of heart structures and measure blood flow. Such intracardial echocardiography (ICE) catheters provide cardiologist and heart surgeons with unique viewing perspectives beneficial to diagnosis and treatment of heart diseases.

To obtain diagnostically useful images, an ultrasound imaging catheter can be positioned next to or within the vessels and chambers of the heart. Typically, the catheter is introduced into a patient through the femoral, subclavian or jugular veins and maneuvered into the right atrium. From there an ultrasound imaging catheter can image the heart anatomy including both left and right atriums, ventricles, the valves, and the atrial and ventricular septal walls. The catheter can also be advanced through the tricuspid valve into the right ventricle from which the right and left ventricles, the septum, the valves and the left atrium may be imaged.

Traditionally there have been two basic methods for positioning ultrasound imaging catheters within the chambers of the heart. In the first method a guide wire is threaded through the patient's vascular structure via catheterization and under fluoroscopy until the distal end reaches a proper position for imaging. A sheath is then extended over the guide wire. Finally, the guide wire is withdrawn and the ultrasound imaging catheter inserted into the sheath. Held in relative position by the sheath, the imaging catheter can be advanced to penetrate deeper into the heart or rotated in order to scan of the heart.

The second method uses a steerable ultrasound imaging catheter to maneuver the catheter into position without the use of a guide wire. An example of a steerable ultrasound imaging catheter 1 is provided in FIGS. 1 and 2. Such steerable catheters 1 included a bendable portion 9 near the ultrasound transducer assembly 4 at the distal end of an elongated catheter body 2. Steering is achieved by tensioning a steering cable attached at or near the distal portion and running down the interior of the catheter to a wheel or knob in the handle 7. When the steering cable is tensioned while the catheter shaft is restrained, the tip will deflect resulting in a bend near the distal end of the catheter as illustrated in FIG. 2. Alternatively, the steering cable may be restrained while the shaft portion 2 is advanced distally, producing the same effect. Typically the induced bend has a radius of curvature of about four inches within an arch defining a plane of fixed orientation with respect to the catheter body 2 and handle 7. The catheter shaft (2) can also be rotated clockwise or counterclockwise to direct the ultrasound transducer face in the desired direction. By rotating the catheter shaft and bending the distal curve 9 the transducer face can be directed as needed. Electrical/signal coaxial cables to/from the ultrasound transducer assembly 4 pass through the catheter body 2 and through the handle 7 to exit as a cable 8 for connection to ultrasound imaging equipment. By being able to bend the distal portion 9 of the catheter, the catheter body 2 can be maneuvered through the patient's vein and into heart chambers without the need for the extra time and steps required by the guide wire and sheath catheterization method.

While the steerable ultrasound catheter obviates the need for a sheath and guide wire, the viewing angle of the ultrasound imaging catheter is restricted due to the bend 9 in the catheter that must be made to properly position the ultrasound imaging assembly 4 within a heart chamber. Rotating the catheter shaft by rotating the handle would cause the ultrasound imaging assembly 4 to swing about. As the transducer face is linear and parallel to the catheter shaft, and because the two directional controls are limited, the, current design steerable ultrasound catheters provide a limited three-dimensional viewing perspective.

SUMMARY OF THE INVENTION

The various embodiments provide an ultrasound imaging catheter with a pivoting head portion which enables the ultrasound imaging transducer array to be pivoted about a hinge with a near-zero radius of curvature. The pivot motion of the ultrasound imaging transducer array is controlled from a handle, such as by pivot cables connected to a control wheel in the handle. Pivoting the ultrasound imaging transducer array through a large angle, such as 90° from the centerline of the catheter, enables clinicians to obtain intracardiac ultrasound images from different perspectives without repositioning the catheter itself. In an embodiment, the ultrasound imaging transducer array is capable of being pivoted plus and minus 90° from a center line position (i.e., parallel to the main axis of the catheter). In an embodiment, the catheter may also be steerable including a capability of bending a distal portion of the catheter through a finite radius of curvature by steering cables controlled from the handle. By combining bending of the catheter with pivoting of the transducer head, greater viewing perspectives can be provided. Embodiments include a handle assembly featuring two control actuators for controlling the steering and pivoting mechanisms of the attached catheter. The various embodiments are not necessarily limited to ultrasound imaging catheters, and may be implemented in any catheter that may benefit from having a distal tip capable of pivoting about a hinge.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain features of the invention.

FIG. 1 is a perspective view of a prior art steerable ultrasound catheter.

FIG. 2 is a perspective view of the steerable ultrasound catheter depicted in FIG. 1 with a bend induced in a distal portion.

DETAILED DESCRIPTION

Figure 3:
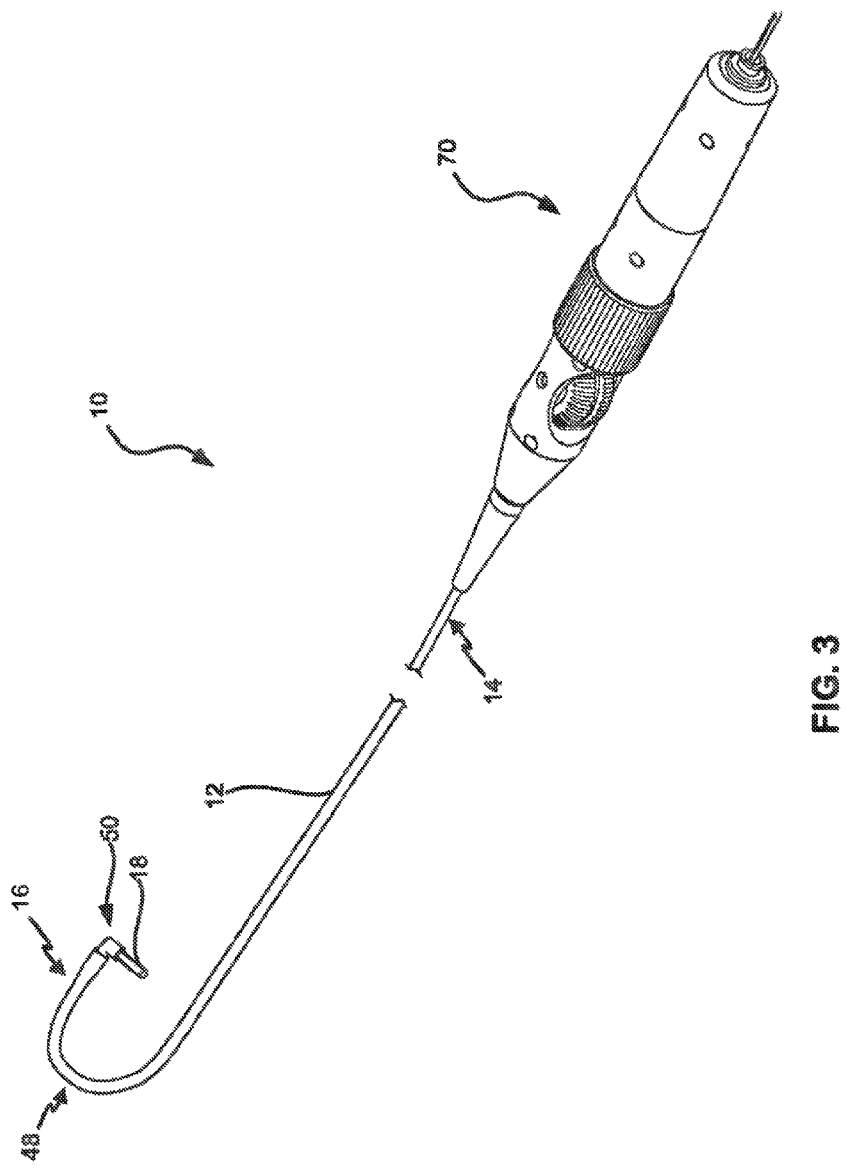
FIG. 3 is a perspective view of an embodiment of the present invention.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

As used herein, the terms "about" or "approximately" for any numerical values or ranges indicates a suitable dimensional tolerance that allows the part or collection of components to function for its intended purpose as described herein. Also, as used herein, the terms "patient," "host" and "subject" refer to any human or animal subject and are not intended to limit the systems or methods to human use, although use of the subject invention in a human patient represents a preferred embodiment.

As used herein, the term "catheter" is used as a general reference to any elongated tubular assembly which may be introduced into an animal or human for medical purposes. Accordingly, references to catheters are not intended to limit the scope of the invention or the claims to any particular forms of catheters, known catheter systems or other subcutaneous medical probes.

Steerable ultrasound catheters known in the art limit the degree to which the ultrasound imaging transducer array can be rotated once positioned within a patient's heart. For example, it can be seen in FIG. 20 that once the ultrasound imaging catheter 12 has been positioned within the right ventricle 302, the bend in a bendable portion 48 of the catheter required to pass the transducer array 18 through the tricuspid valve 309 limits the degree to which the catheter can be turned to adjust viewing angles. In this position, further manipulation of the catheter 12, such as a rotation, would cause the transducer array portion 18 to stress the tricuspid valve 309 or impact other heart structures. Consequently, when a steerable ultrasound imaging catheter is positioned to image a region of interest, there is a limited ability to obtain images along different imaging planes without significant movement and repositioning of the catheter. This limits a clinician's view of a structure of interest to narrow two-dimension (2D) image slices. However, for many procedures there would be diagnostic benefits if the clinician could obtain images of a structure of interest on orthogonal imaging planes. For example, by imaging a ventricle along two orthogonal imaging planes, an accurate estimate of ventricle volume can quickly be obtained.

In order to overcome the limitations of the prior art, the various embodiments provide a pivot mechanism coupled to the ultrasound transducer array assembly which is configured to enable a clinician to pivot the transducer array through a sharp angle, such as 90° in either direction with a zero radius of curvature. The embodiments include a hinge or pivot joint configured so that the path of the transducer array through the full range of rotation is constrained to a plane with respect to the catheter. The pivot motion and rotational position of the transducer array with respect to the catheter can be controlled by a pivot cable connected to a control actuator (e.g., a wheel coupled to a spool) in a handle assembly. The control actuator, handle assembly and pivot head are configured so that a clinician can accurately control the angle of rotation of the transducer array. The catheter assembly may or may not be steerable. If the catheter assembly is steerable, a separate steering mechanism is provided in the handle assembly and coupled to a bendable portion of the catheter which is separate from the pivot head assembly. So configured, the various embodiments enable a clinician to steer the catheter through a patient's vascular structure in order to place the transducer array in a proper position within the patient's body to image a structure of interest, and then pivot the transducer array in order to obtain different imaging perspectives without otherwise repositioning the catheter.

An embodiment of a steerable catheter assembly 10 is illustrated in FIG. 3. In this embodiment, the steerable catheter assembly 10 includes an elongated tubular member 12 coupled to a transducer array assembly 18 at the distal end, and to a handle assembly 70 at the proximal end. The steerable catheter assembly 10 includes a bendable portion 48 which can be controlled from the handle assembly 70 in order to steer the catheter through a patient's vascular structure. Coupled between the transducer array assembly 18 and the distal end of the elongated tubular member 12 is a pivot head assembly 50. The pivot head assembly 50 permits the transducer array assembly 18 to be pivoted through an angle, such as approximately 90° as illustrated in FIG. 3.

Figure 4:
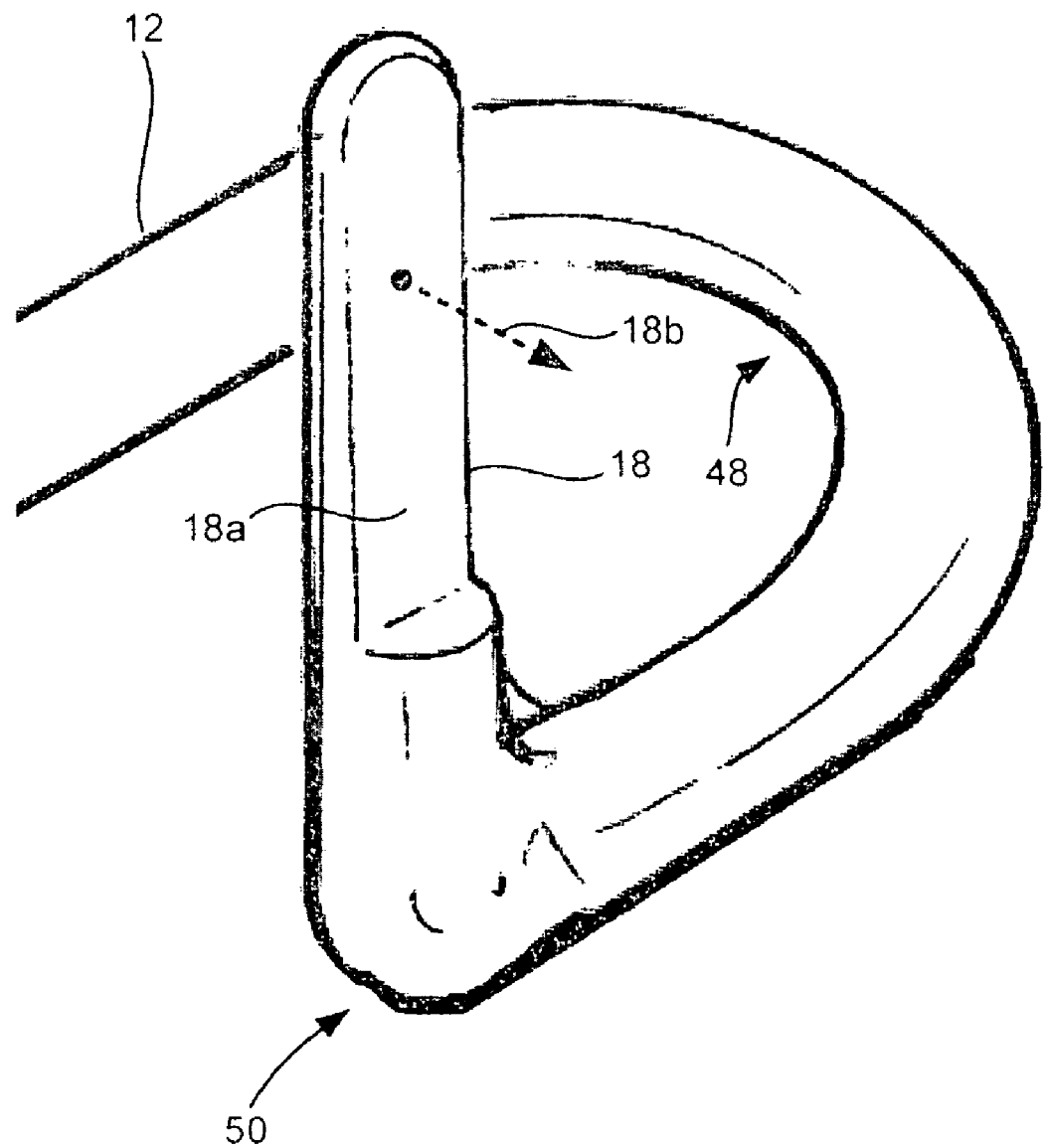
FIG. 4 is a detail of a distal portion of the embodiment illustrated in FIG. 3.

In a preferred embodiment, the pivot head assembly is positioned at or just beyond the distal end of a bendable portion 48 of the elongated tubular member 12 as illustrated in FIG. 4. As mentioned above, the pivot head assembly 50 includes a hinge (illustrated in subsequent figures) so that the transducer array assembly 18 can be rotated or pivoted with a zero radius of curvature. In contrast, the bendable portion 48 has a radius of curvature that typically will be approximately 4 inches, which is a dimension determined by the typical path requirements of the human vascular structure leading to the heart. In an embodiment illustrated in FIG. 4, the pivot head assembly 50 may be configured so that the rotational plane through which the transducer array 18 pivots is orthogonal to the plane of curvature of the bendable portion 48 of the elongated tubular member 12. In other embodiments, the plane of rotation of the transducer array assembly 18 may be parallel to the plane of curvature of the bendable portion of the elongated tubular member 12 or at an angle between parallel and perpendicular. As FIG. 4 illustrates, the pivot head assembly 50 permits the transducer array assembly 18 to be positioned and oriented in a manner that is not achievable using known steerable catheters.

The embodiment illustrated in FIG. 4 features a transducer array assembly 18 having a flat face 18a. In other embodiments, the transducer array assembly 18 includes a cover portion which presents a circular or ovoid cross-section. Thus, the flat face 18a shown in FIG. 4 is but one embodiment. Nevertheless, this illustration demonstrates a feature of transducer array assemblies typical in ultrasound imaging catheters. Due to the severe space restrictions imposed by the small diameter of intracardiac catheters, the ultrasound imaging transducer is typically limited to a linear phased array made up of several individual transducer elements, such as 64 transducers. The transducers have a flat surface from which sound is omitted and echoed sound is received. As is well known in the art, the individual transducer elements are pulsed by an ultrasound control system so that the emitted sound waves are constructively combined into a primary beam. By varying the time at which each transducer element is pulsed, the ultrasound control system can cause the transducer array to omit narrow sound beams which can be swept through an arc in order to obtain a 2D image. As a result, the transducer array emits ultrasound along a plane which is perpendicular to the face of the transducer arrays. Thus, as illustrated by the dashed arrow 18b in FIG. 4, the transducer array assembly 18 emits sound along a plane which is perpendicular to the flat face 18a the assembly. Thus, when the transducer array assembly 18 is rotated about the pivot head assembly 50 to 90° from the catheter centerline as illustrated in FIG. 4, the plane of the 2D ultrasound image is orthogonal to the plane of the 2-D ultrasound image that will be generated when the ultrasound imaging array 18 is positioned at a zero angle of rotation (i.e., parallel to the centerline of the elongated tubular array 12).

It should be noted that FIG. 4 illustrates just one example embodiment, specifically one in which the ultrasound imaging plane is perpendicular to the plane of rotation (i.e., parallel to the axis of rotation of the pivot head assembly 50). In other embodiments, the transducer array assembly 18 may be configured to image along planes at a different angle with respect to the plane of rotation, an example of which is described more fully below with reference to FIGS. 19A-19C.

Before describing further details regarding the pivot head assembly, the characteristics and construction of the elongated tubular member 12 and bendable portion 48 (i.e., the portion of the catheter assembly between the handle assembly 70 and the pivot head assembly 50) will be described with reference to FIG. 5A through FIG. 8.

Many catheters used in intravascular applications are about 90 cm in insertable length. The elongated tubular member 12 of the catheter assembly 10 of the various embodiments can range from about 80 cm in insertable length to about 120 cm in insertable length. In one embodiment, the elongated tubular member 12 of the catheter assembly 10 is about 90 cm in length. Some applications, such as veterinarian imaging of large animals (e.g., horses), will benefit from catheters having a longer insertable length. Thus, the elongated tubular member 12 of the catheter assembly 10, can also be about 100 cm, about 110 cm, about 120 cm, or even longer in length.

Most catheters used in intravascular applications, particularly those with ultrasound transducers, are at least about 10 French in diameter. The electronics and wires needed for ultrasound transducer arrays have made it impractical and expensive to reduce the size of such catheters below about 10 French. Nevertheless, there are benefits in reducing the diameter of the catheter, and technology advances may enable the electronics and control structures to be further reduced in size. The bundling arrangement of the coaxial cables, steering and pivot cables and steering and pivot mechanisms described in more detail below, make it possible to effectively reduce the diameter below about 10 French, to about 9 French, about 8 French, about 7 French, or even about 6 French (approximately 2 mm). Accordingly, the elongated tubular member 12 of the catheter assembly 10 can range from about 6 to about 12 French in diameter.

Referring to FIG. 3, the catheter assembly 10 includes an elongated tubular member 12 having a proximal end 14 and a distal end 16. In an embodiment, the material for the tubular member is extruded polyether block amide of the type sold by Atochem North America, Inc. under the trademark PEBAX. Depending on the intended use of the catheter, the tubular member can be made of PEBAX 7233 having a Shore Durometer hardness of approximately 72 D, PEBAX 7033 having a Shore Durometer hardness of approximately 69 D, PEBAX 6333 having a Shore Durometer hardness of approximately 63 D, PEBAX 5533 having a Shore Durometer hardness of 55 D, PEBAX 4033 having a Shore Durometer hardness of 40 D, PEBAX 3533 having a Shore Durometer hardness of 35 D, or PEBAX 2533 having a Shore Durometer hardness of 25 D. Different sections along the length of the tubular member 12 can be made from different grades of PEBAX to give the catheter assembly 10 variable flexibility along its length. The tubular member 12 can also be formed from other materials, such as other polymeric materials that have excellent shape retention characteristics. For example, the tubular member 12 can be made of polyethylene, silicone rubber, or plasticized PVC.

Located at the distal end of the elongated tubular member 12 is the pivot head assembly 50 and the ultrasound transducer assembly 18. The transducer assembly 18 can be formed from an array of individual ultrasound elements as is well known in the art. There may be forty-eight or more such ultrasound elements 20 that form the transducer assembly 18. In a preferred embodiment the transducer assembly 18 is a sixty-four element linear phased array ultrasound imaging sensor. One example of an ultrasound transducer that can be incorporated into the catheter assembly 10 is the ultrasound imaging catheter marketed under the trademark ViewFlex® by EP MedSystems, Inc. of West Berlin, N.J. In addition to the ultrasound transducers and associated circuitry, the transducer assembly 18 may include other electronics, such as a temperature sensor (e.g., a thermistor) as disclosed in U.S. Pat. No. 6,908,434 entitled "Ultrasound Imaging Catheter Isolation System With A Temperature Sensor," the entire contents of which are hereby incorporated by reference.

The elongated tubular member 12 may include a section that is configured to preferentially bend or bend in response to tensions applied by steering cables so as to provide improved catheter maneuverability and to decrease the risk of damage to an anatomical structure, such as a blood vessel or heart chamber during advancement of the catheter tip. By including a flexible tubular portion 22 within or attached to the elongated tubular member 12, the catheter assembly 10 will tend to bend at that more flexible portion when a force is applied (e.g., from encountering an obstruction or from tension applied to an internal steering cable). Thus, for example, the Shore Durometer hardness of the material forming the flexible tubular portion 22 can be about 35 D to 63 D, or more preferably about 40 D to about 55 D. Different grades of PEBAX as described above, for example, can be used to make the flexible portion 22 have the desired flexibility. In some embodiments, a bendable portion subassembly 48 illustrated in FIGS. 6A-6E is configured with a flexible tubular portion 22 and other structures so that a bend in that portion can be controlled by tension applied through steering cables 42, 44. In other embodiments, a flexible tubular portion 22 is included in or attached to the elongated tubular member 12 so that when the catheter assembly is advanced through a patient's vascular structure, the tubular member 12 bends freely at the flexible tubular portion 22 when the distal tip of the transducer assembly 18 contacts a vessel wall.

Located at the proximal end 14 of the tubular member 12 is a handle assembly 70. As described more fully below with reference to FIGS. 14-17 the handle assembly 70 can include a steering control mechanism such as a rotatable control knob, handle or wheel, slide actuator, or other suitable manipulating member that controls tension applied to one or more steering cables 42, 44 that extend through the lumen of the tubular member 12 to a point near the distal end of a bendable portion subassembly 48 for controlling the bending movement of the catheter proximate the transducer assembly.

Before assembling the catheter portion of the catheter assembly 10, the transducer array assembly 18 is coupled to the pivot head assembly 50 as described in more detail below with reference to FIGS. 9-11. This creates a pivoting transducer assembly 67, illustrated in FIGS. 7 and 8, from which extends a bundled 30 of coaxial cables, a pivot cable conduit 60 including one or more pivot cables 62, 64, and any other electrical leads connected to the transducer array assembly 18. This assembly can then be coupled to the bendable portion 48 which is coupled to the elongated tubular member 12 as described more fully below.

Figure 5A:
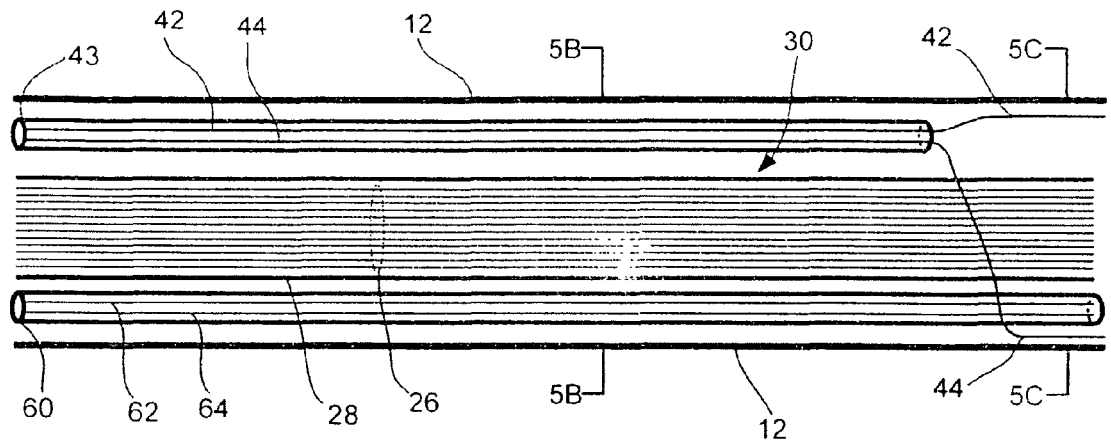
FIGS. 5A-5C are cross-sectional views of a portion of the embodiment illustrated in FIG. 3.
Figure 5B:
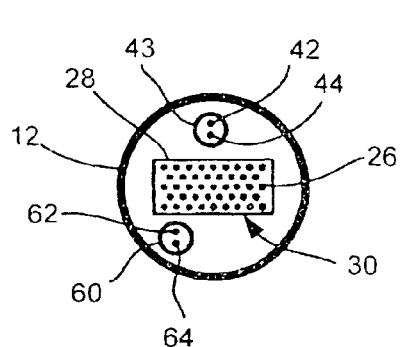
Figure 5C:
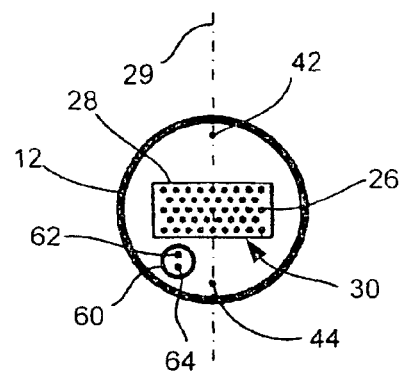

Details of a portion of the structures contained within the elongated tubular member 12 are illustrated in FIG. 5A which shows a lateral cross section of the tubular member 12. These structures are also illustrated in FIGS. 5B and 5C which show cross sectional views of the tubular member 12 at the indicated cross sections 5B and 5C, respectively. The elongated tubular member 12 is hollow and has a lumen extending therethrough. Nested within the lumen of the elongated tubular member 12 is a bundle 30 of electrical cables 26, a steering cable conduit 43 for one or more steering cables 42, 44, and a pivot cable conduit 60 including one or more pivot cables 62, 64. In the illustrated embodiment, the electrical cables 26 are coaxial cables suitable for use with ultrasound transducers. The cable bundle 30 is formed by bundling together all of the coaxial cables 26 that are necessary to operate the transducer assembly 18. The bundle 30 will preferably carry a corresponding number of coaxial cables 26 to match the number of elements in the transducer. For example, if the transducer assembly 18 is a forty-eight element transducer, then generally forty-eight coaxial cables 26 will form the bundle 30, and if the transducer assembly 18 is a sixty-four element transducer, then generally sixty-four coaxial cables 26 will form the bundle 30. In one embodiment, for example, the transducer assembly 18 can have a sixty-four element parallel drive phased array, in which case the bundle 30 has at least sixty-four coaxial cables 26. It should be appreciated, however, that the cross-sectional diameter of the catheter assembly 10 can be reduced by reducing the number of coaxial cables 26 and, correspondingly, the number of elements in the transducer assembly 18. It should be appreciated that none of the embodiments described herein are limited by the number of elements in the transducer assembly 18. It should be further appreciated that in other forms of catheters, such as ablation and electrophysiology catheter embodiments, the electrical cables 26 will be configured as appropriate for connecting sensor or therapy elements to external equipment, and may be coaxial, twisted pair, dual stranded or single stranded electrical conducting cables as appropriate to such applications.

In the embodiment shown in FIG. 5A, the coaxial cables 26 are bundled within a protective sheath 28 forming an ovular or rectangular cross-section. The protective sheath 28 may be formed from polyamide or PVC. The bundle 30 can include various types of filler material (not shown), such as Pebax, to provide the catheter assembly 10 with different shape retention and rigidity characteristics. In another embodiment, the coaxial cables are spun together along with one or more filler materials to form a bundle 30 having an ovular or rectangular cross-section.

As shown in FIGS. 5A through 5C, a hollow steering cable conduit 43 includes a lumen that carries one or more steering cables 42 and 44. Similarly, a hollow pivot cable conduit 60 includes a lumen that carries one or more pivot cables 62, 64. It should be appreciated that in embodiments that do not include steering capabilities (e.g., catheters which make use of a flexible tubular portion 22 without steering capability) there will be no need for the steering cable conduit 43 or the steering cables 42, 44. In the embodiment shown in FIGS. 5A through 5C, the steering cables 42 and 44 are nested together and the pivot cables are nested together along most of the length of the elongated tubular member 12. Nesting the steering and pivot cables together along the length of the elongated tubular member 12 insurers that a bend in the proximal end of the elongated flexible member 12 will have minimal or no affect on the steering at the distal end of the catheter. If the steering cables and pivot cables are not nested together, a kink or bend at any point along the length of the catheter assembly 10, such as near the proximal end 14, could cause a corresponding bend at the distal end of the catheter assembly 10 or an unintended pivoting of the transducer array assembly 18. This is because a steering and/or pivot cable on the outside of the bend will be more displaced by the bend than a steering and/or pivot cable on the inside of the bend, causing an unintentional pulling force by the cables.

Near the distal end of the steering cable conduit 43, the steering cables 42 and 44 may diverge as illustrated at cross section 5C. Steering cable 42 remains on one side of the bundle 30, while steering cable 44 is threaded around the bundle 30 to the other side thereof. When a pulling force is applied to one steering cable 42, that steering cable 42 applies a corresponding pulling force to one side of the distal end of the elongated tubular member 12, thus bending the distal end of the catheter assembly 10 in one direction along a plane identified by line 29 shown in FIG. 5C. In addition to the placement of steering cables 42, 44 on opposite sides of the elongated tubular member 12, the rectangular or oval shape of the cable bundle 30 helps constrain the bending of the bendable portion 48. As a result of the ovular or rectangular cross section of the bundle 30, the bundle 30 will preferentially or selectively bend in two directions that are approximately 180° opposite each other along the plane identified by line 29 in FIG. 5C. That is, under an applied force, the cable bundle 30 will bend about the longer sides of the oval or rectangle and resist bending along the shorter sides.

In an embodiment, shape memory filler material may be incorporated into the bundle 30 to help retain a bend until a pulling force applied to the steering cable 44 applies an opposite force to the distal end of the elongated tubular member 12 causing the bendable portion 48 to return to a straight configuration or to another bend configuration within the bending plane 29. In another embodiment, shape memory filler material is not incorporated into the bundle 30, and a pulling force must be maintained in order to maintain the bend at the distal end of the catheter assembly 10.

The ovular or rectangular cross-section of the bundle 30 provides ample space on the long sides of the rectangle for additional wiring, such as the steering cable conduit 43, the pivot cable conduit 60, working elements or tools, and wiring from additional sensors, such as for example temperature sensors (e.g., a thermister) and/or electrodes (e.g., electrophysiology electrodes).

Figure 6D:
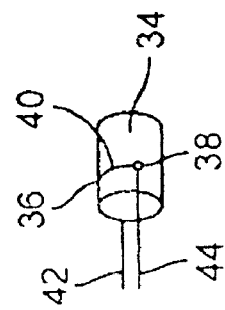
FIGS. 6A-6E are perspective views of components within a portion of the embodiment illustrated in FIG. 3.
Figure 6E:
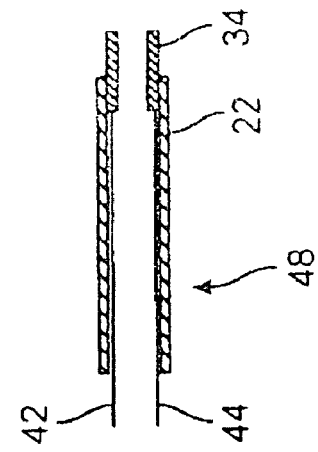
Figure 6C:
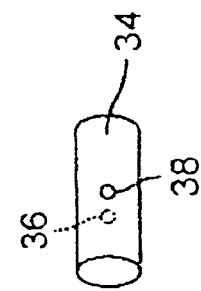
Figure 6A:
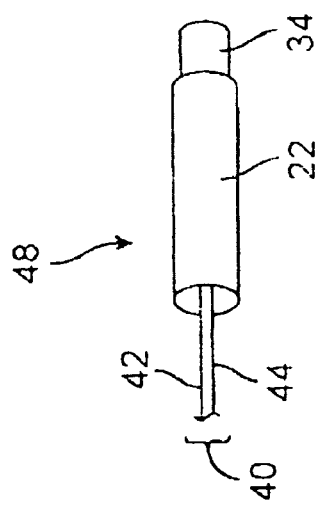
Figure 6B:
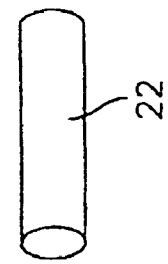

FIGS. 6A through 6E illustrate the bending portion subassembly 48 of the catheter assembly 10 proximal the transducer assembly 18. This bending portion subassembly 48 provides the attachment point for the steering cables 42, 44 and the flexible tubular member 22 that enable inducing a controllable bend in the catheter assembly 10. As illustrated in FIG. 6A, the bending portion subassembly 48 includes a small hollow cylinder 34 coupled to the flexible tubular member 22 (shown in FIG. 6B) at the distal end. The flexible tubular member 22 may be, for example, silicon, Pebax or polyethylene with an outside diameter of about 9 French and about 1 to about 8 inches in length.

As shown in FIG. 6C the hollow cylinder 34 includes holes 36 and 38 formed in the outer wall to which a steering cable 40 can be connected. In the embodiment illustrated in FIG. 6D, one steering cable 40 passes through the interior of the cylinder 34, out of the hole 36, around the outer circumference of the cylinder 34 and back through the hole 38 to the interior or lumen of the cylinder 34. As a result, two steering cables 42, 44 are essentially formed from the opposite ends 42 and 44 of a single steering cable 40. These two steering cable ends 42 and 44 are lead down through the lumen of the elongated tubular member 12 to the handle assembly 70, where the steering cables are coupled to a steering mechanism described below with reference to FIGS. 14-17. If the steering mechanism asserts a pulling force against one of the two steering cables, such as steering cable 42, for example, the steering cable 42 pulls on the cylinder 34 at hole 36 causing the cylinder to twist toward the tensioned steering cable 42. The force on the cylinder 34 causes the flexible tubular member 22 to bend in a first direction towards steering cable 42. As a result, the distal portion of the catheter assembly 10 forms a bend in the first direction. When the steering mechanism applies a pulling force on the other steering cable 44, the steering cable 44 pulls on the cylinder 34 on the side of the other hole 38, causing the flexible tubular member 22 to bend in a second direction opposite the first direction toward steering cable 44.

In an embodiment, the two steering cable ends 42 and 44 are connected, such as by fusing or tying the ends, forming a single, elongated loop within the catheter assembly 10. In this embodiment, the steering cable elongated loop may be wrapped around a pulley or spindle, for example, in the steering mechanism within the handle assembly 70 which can be turned, such as by the operator turning an attached handle or wheel, to exert a pulling force on one side of the elongated loop while letting out the other side of the elongated loop.

In an alternative embodiment (not shown), two separate steering cables are used rather than looping one steering cable over cylinder 34. A distal end of the first steering cable is threaded through the cylinder 34 and out the hole 36. The distal end of the first steering cable is secured to the outer wall of the cylinder 34 adjacent the hole 36 by an adhesive, enlarged knot, wrapping it around a screw fastened to the cylinder 34 or other means. A distal end of the second steering cable is threaded through the cylinder 34 and out the hole 38. The distal end of the second steering cable is secured to the outer wall of the cylinder 34 adjacent the hole 38 by an adhesive, enlarged knot, wrapping it around a screw fastened to the cylinder 34 or other means. The proximal ends of each of the steering cables are threaded through the lumen of the elongated tubular member 12, such as through the steering cable conduit 43, out the proximal end of the elongated tubular member 12, and connected to the steering mechanism within the handle assembly 70.

The one or more steering cables 42, 44 may comprise a strand, wire, and/or thread, and is preferably made from low profile, durable, non-elastic and non-conducting material. For example, the steering cable(s) can be made of synthetic materials, such as nylon or similar synthetic fibers, or plastics material, such as urethane, Teflon®, Kynar®, Kevlar®, polyethylene, multistranded nylon, or gel-spun polyethylene fibers. For example, the steering cables may be multistranded Spectra® brand nylon line sold as Spiderwire® fishing line (10 lbs. test).

Once the steering cable 40 is assembled on the cylinder 34, the flexible tubular member 22 is connected to the cylinder 34, by inserting the proximal end of the cylinder 34 through the distal end of the flexible tubular member 22 as illustrated in FIG. 6E. Thereafter, an adhesive or fastener (not shown) may be applied to the area where the steering cable 40 abuts the distal end of the flexible tubular member 22 to fix the steering cable 40 and cylinder 34 in place against the flexible tubular member 22. Alternatively, the flexible tubular member 22 and cylinder 34 may be frictionally engaged, with the opposite ends of the steering cable 40 immovably trapped between the lumen of the flexible tubular member 22 and the outer wall of the cylinder 34.

Figure 7:
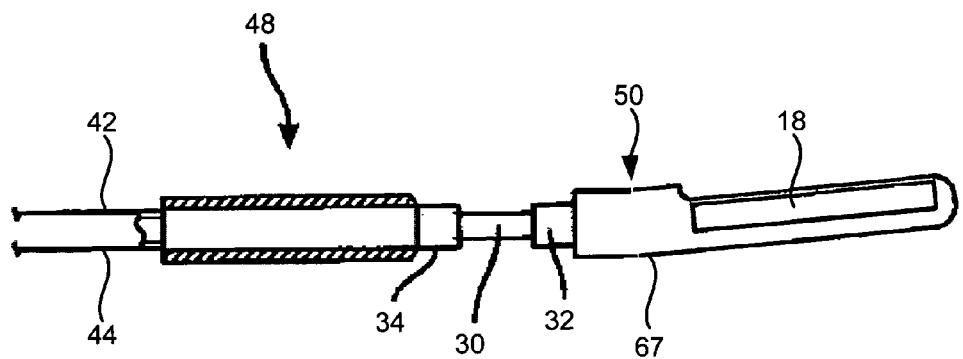
FIG. 7 is a side view of the distal portion of the catheter embodiment illustrated in FIG. 3 showing a stage of assembly.
Figure 8:
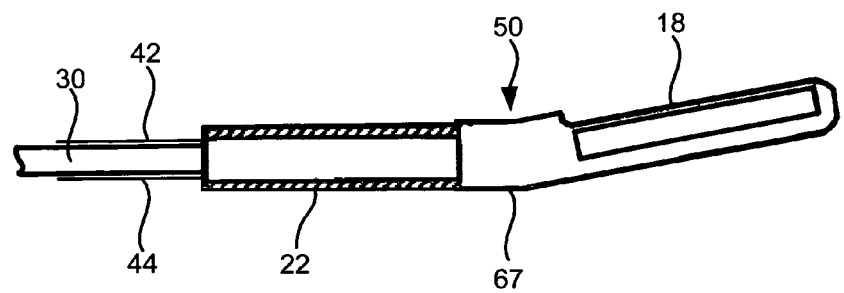
FIG. 8 is a side view of the distal portion illustrated in FIG. 7 showing the portion after assembly.

Once the steering cable 40, cylinder 34 and flexible tubular member 22 are combined to form the bending portion subassembly 48, the subassembly is slid over the proximal end of the cable bundle 30 and is moved toward the ultrasound transducer assembly 18 as shown in FIGS. 7 and 8. As the parts are assembled, the distal end of the cylinder 34 may fit over a support cylinder 32 coupled to the proximal end of the pivot head assembly 50. The pivot head assembly 50 may include a recessed fitting to receive the cylinder 34.

During assembly the steering cable end 42 is positioned so that it is aligned with one of the long sides of the ovular or rectangular of the cable bundle 30. Similarly, the other steering cable end 44 is positioned so that it is aligned with the other long side of the ovular or rectangular cross-section cable bundle 30. This can be achieved by aligning the holes 36 and 38 with the long sides of the cable bundle 30 when the subassembly 48 is slid over the cable bundle 30 and steering cable ends 42 and 44 and connected to the transducer assembly 18.

To connect the proximal end of the flexible tubular member 22 to the distal end of the elongated tubular member 12, a cylindrical connector member (not shown) similar to the cylinder 34 but without the holes in the side walls can be guided over the proximal ends of the cable bundle 30 and steering cable ends 42 and 44 and into the lumen of the flexible tubular member 22. The outer diameter of the cylindrical connector member can be just slightly smaller than the diameter of the lumen of the flexible tubular member 22 so that it can slide into the flexible tubular member 22.

The last step of assembling the catheter portion of the catheter assembly 10 involves the elongated tubular member 12, which forms the outer surface of the catheter assembly 10. The elongated shaft 12 has an outer diameter of about 6 French to about 9 French, and an inner diameter large enough to encompass the cable bundle 30, steering cable and pivot cable conduits 43, 60, and any other included wires (not shown). The elongated tubular member 12 is guided over the cable bundle 30 and cable conduits 43, 60. The elongated tubular member 12 is pushed forward until its distal end over the cylindrical connector member and abuts the proximal end of the flexible tubular member 22. Once in place, the distal end of the cylindrical connector member may be secured to the flexible tubular member 22 using an adhesive on the outer wall of the cylindrical connector member, on the inner luminal wall of the flexible tubular member 22 or at the interface between the two tubular members. Alternatively, the cylindrical connector member may be secured to the inner luminal wall of the flexible tubular member 22 through friction or mechanical collar or latch (not shown).

Figure 9:
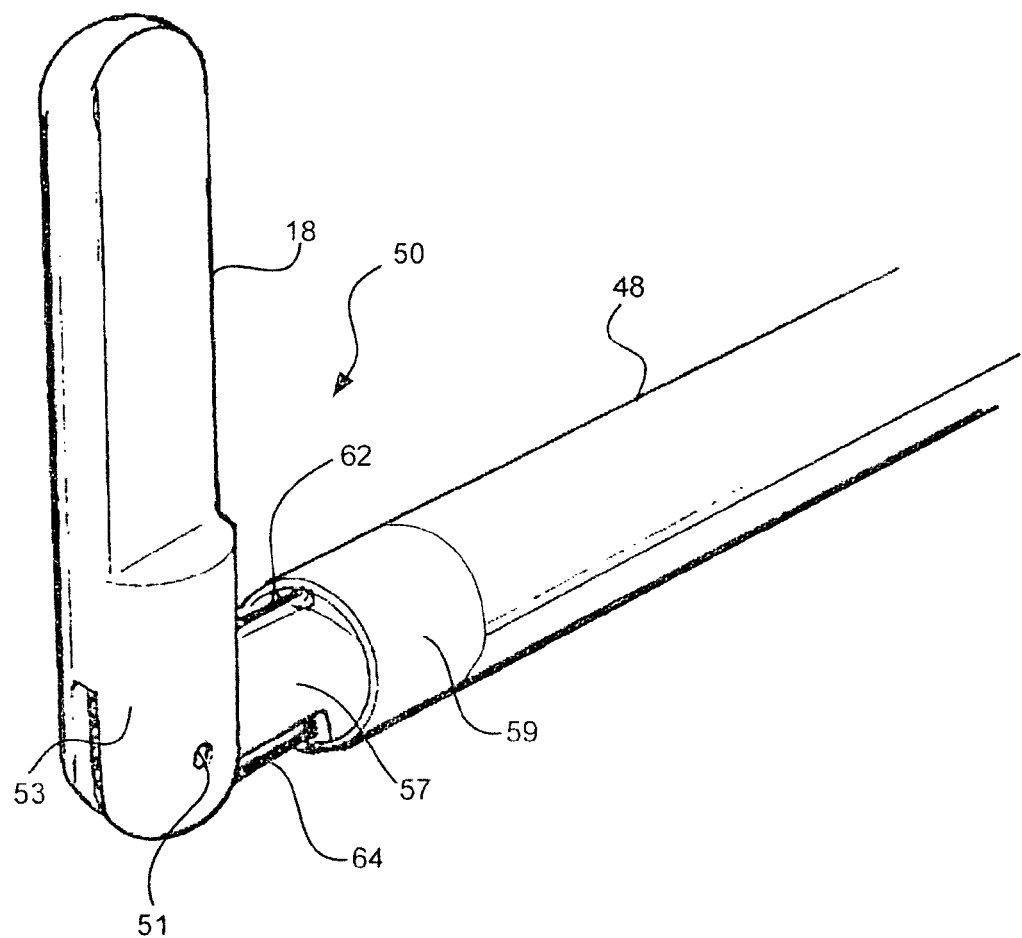
FIG. 9 is a perspective view of an embodiment of the pivot head assembly.

Details of the pivot head assembly 50 are illustrated in FIGS. 9-13. The pivot head assembly 50 includes a hinge or pivot point, an example of which is illustrated in FIG. 9. In this embodiment, the hinge comprises a pintle 51 forming a flexible joint between an inner hinge support member 57 coupled to a base member 59 and outer hinge support members 53 coupled to a proximal end of the transducer array assembly 18. The hinge may be configured so that the inner hinge support member 57 can slip between the two outer hinge support members 53 with minimal friction but with sufficient lateral support so that the transducer array assembly 18 is constrained to pivot about the pintle 51 within a plane. The two outer hinge support members 53 include a through hole into which the pintle 51 is inserted. The pintle 51 may be held in position in the two outer hinge support members 53 by friction, adhesive, a spring clip, a cap over the holes, or other means. To enable smooth rotation of the transducer array assembly 18 about the pintle 51, a lubricant or a low friction surface, such as Teflon®, may be deposited on the inner surfaces of the two outer hinge support members 53, on a central portion of the pintle 51 and/or on the surfaces of the inner support member. The base member 59 may be configured to couple to the bending portion subassembly 48, such as by fitting over the support cylinder 32 as illustrated in FIGS. 7 and 8. Thus when assembled to the bending portion subassembly 48 the base member may abut the flexible tubular member 22 as illustrated in FIGS. 8 and 9. The bundle 30 of coaxial cables 26 and other electrical wires running from the transducer array assembly 18 are fed between the transducer array assembly 18 and the base member 59 with sufficient play to enable the pivot head to traverse a full 180° (i.e., 90° in either direction from 0° deflection) without binding or disconnecting any cable from the transducer array. The bundle 30 is omitted from FIG. 9 so that the structure of the hinge can be illustrated.

Pivot cables 62, 64 extend from the base member 59 on either side of the inner hinge support member 57. The pivot cables 62, 64 are connected to one or both of the two outer hinge support members 53 so that when one of the pivot cables is placed in tension the pivot head assembly 50 pivots the transducer array 18 about the pintle 51. The pivot cables 62, 64 may comprise a strand, wire, and/or thread, and are preferably made from low profile, durable, non-elastic and non-conducting material. For example, the pivot cables 62, 64 can be made of synthetic materials, such as nylon or similar synthetic fibers, or plastics material, such as urethane, Teflon®, Kynar®, Kevlar®, polyethylene, multistranded nylon, or gel-spun polyethylene fibers. For example, the steering cables may be multistranded Spectra® brand nylon line sold as Spiderwire® fishing line (4-10 lbs. test).

Figure 10:
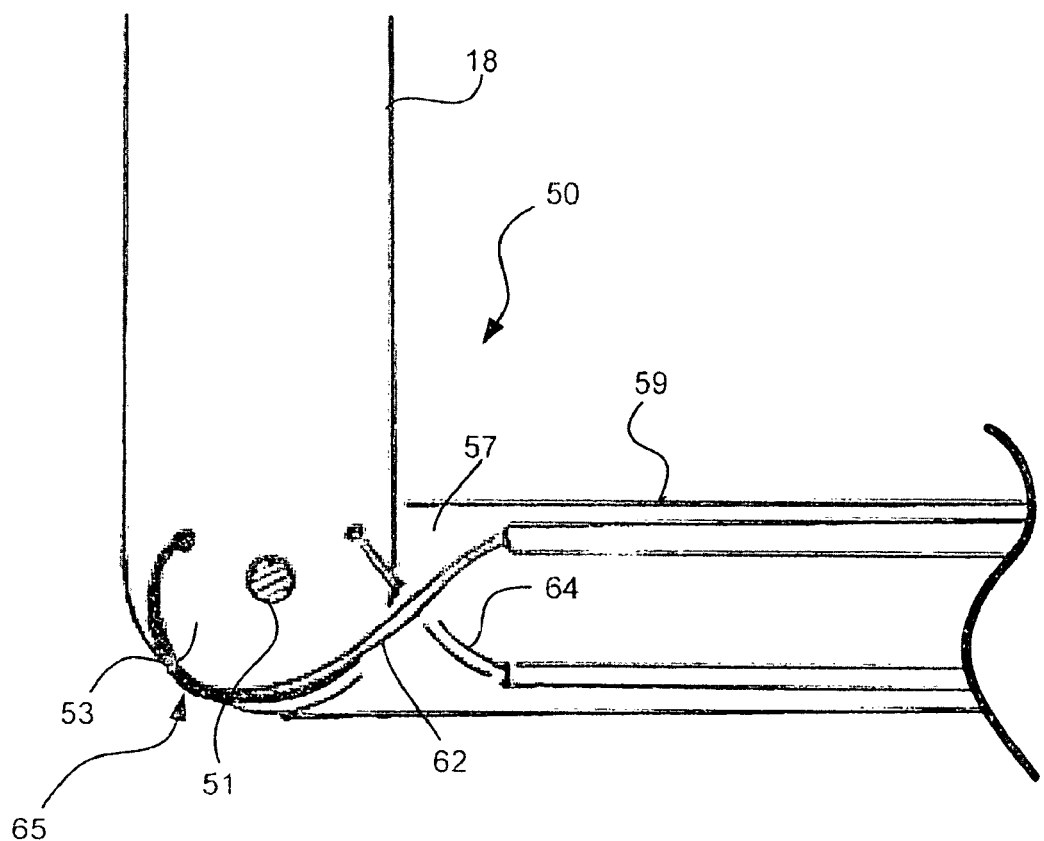
FIG. 10 is a cross-sectional view of the embodiment shown in FIG. 9.

An example of how the pivot cables 62, 64 may be connected to one or both of the two outer hinge support members 53 is shown in FIG. 10. In the illustrated example the pivot cables 62, 64 connect to opposite sides of the two outer hinge support members 53 and loop around the pintle 51 so that a full 180° of rotation can be accomplished by tensioning one or the other of the two pivot cables 62, 64. As can be seen in FIG. 10, tensioning pivot cable 64 causes the transducer array assembly 18 to pivot from 0° deflection to a positive 90° deflection as illustrated. As the transducer assembly 18 deflects from 0° to a positive 90° angle of deflection, the other pivot cable 62 is allowed to loop under one of the two outer hinge support members 53. So positioned, the pivot cable 62 has leverage on the outer hinge support member 53 so that when it is tensioned, the transducer array assembly 18 can be deflected from positive 90° deflection all the way around to −90° deflection. The routing of pivot cables 62, 64 illustrated in FIG. 10 is but one illustration of how pivot cables can be connected to the transducer array assembly 18, and is not intended to be limiting.

Figure 11:
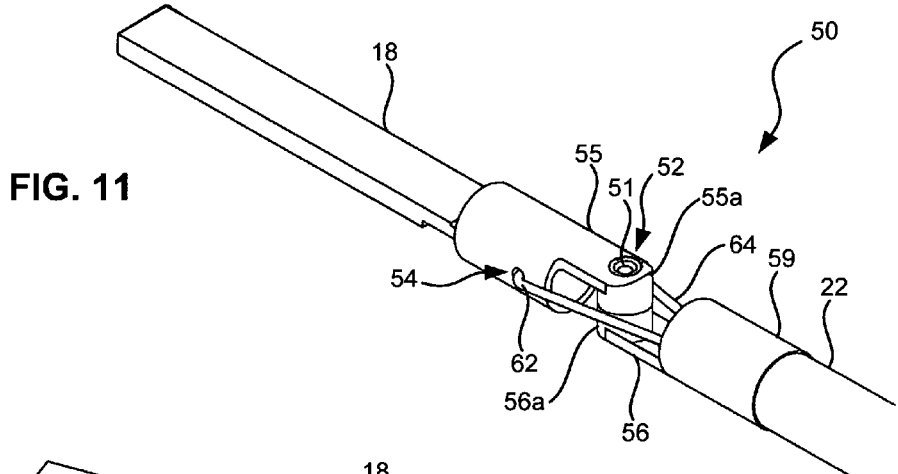
FIGS. 11-13 are perspective views of another embodiment of the pivot head assembly showing different angles of rotation.
Figure 12:
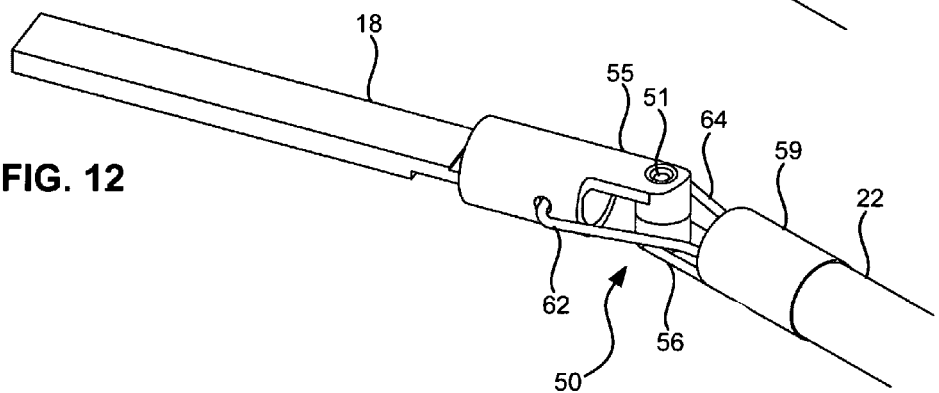
Figure 13:
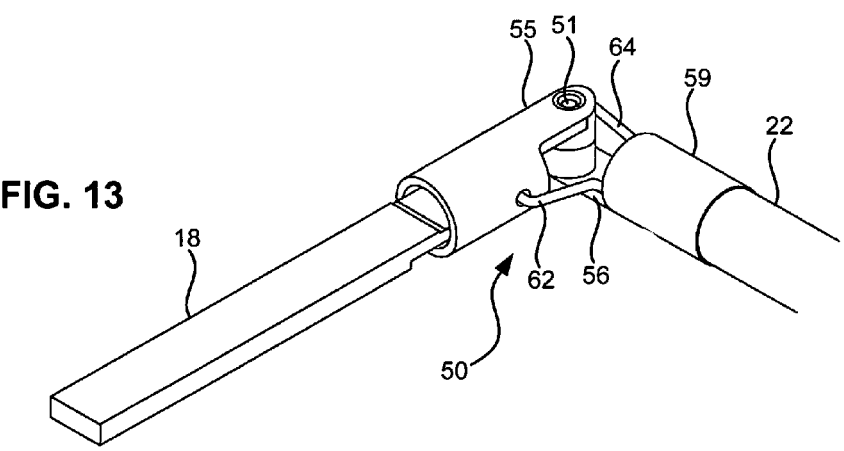

An alternative configuration embodiment for the hinge or pivot joint is illustrated in FIGS. 11-13. Referring to FIG. 11, the hinge in this embodiment is formed from a proximal hinge support member 56 coupled to the base member 59, a distal hinge support member 55 and a pintle 51 positioned within tubular portions 56a and 55a of the proximal hinge support member 56 and distal hinge support member 55, respectively. A through hole 52 in each of the proximal and distal hinge support members 56, 55 is provided to accept the pintle 51 with sufficient clearance to enable low friction rotation, but with sufficient diameter to constrain the rotation of the transducer array assembly 18 to a plane perpendicular to the through hole 52 axis. Lubricant or low friction materials, such as Teflon®, may be provided in the inner surface of the through hole 52, on the surfaces of the pintle 51, and/or the interfacing surfaces between the tubular portions of the proximal and distal hinge support members 56, 55. Once assembled, the pintle 51 may be held in place within the through hole 52 by a spring clip, adhesive, cap, or other known mechanisms for retaining a pin within a hole. In an embodiment, the pintle 51 may be integral to one of the proximal or distal hinge support members 56 or 55 and configured to fit within a through hole 52 within the other support member. As discussed above with regard to FIG. 9, the base member 59 may be configured to easily couple to the rest of the catheter assembly 10 so that the base member 59 abuts the flexible tubular member 22 as illustrated.

The pivot cables 62, 64 may connect to an outer surface of the distal support member 55, such as by being threaded through a hole 54 and secured in place, such as by use of an adhesive, a large knot, or an end cap on the pivot cable 62. Alternatively, the pivot cable 62 may pass through the hole 54, laterally across the distal hinge support member 55 and out a hole (not shown) on the other side to exit as pivot cable 64. So configured, tensioning of one pivot cable 62, 64 will cause the distal portion of the pivot head assembly to rotate in the direction of the tensioned cable. This is illustrated in FIGS. 12 and 13 which show the transducer array assembly 18 rotating through an angle in response to tension applied to pivot cable 62. FIGS. 11-13 show the pivot cables 62, 64 exiting the base member 59 on the same side as their connection to the distal hinge support member 55. However, the pivot cables may cross within the space between the hinge point in the base member 59 so that they enter the base member 59 on opposite sides similar to the arrangement illustrated in FIG. 10.

The coaxial cable bundle 30 is omitted from FIGS. 11-13 so that the structural details of the pivot head assembly 50 can be seen. However, the cable bundle 30 will be positioned to pass around the pivot joint (i.e., elements 51, 55a and 56a) with sufficient slack so that the transducer array assembly 18 can be rotated through a full 180° without tensioning the cable bundle 30.

As discussed above, the transducer array assembly 18 and pivot head assembly 50 may be assembled as a first step in the assembly of the catheter assembly 10. Cables leading from the transducer array assembly 18 are threaded around the pivot joint and through the base member 59. Pivot cables 62, 64 are attached to the distal hinge support member 55 and threaded through the base member 59. The hinge is assembled by positioning the hinge members (either the inner and outer hinge support members 53, 57, or the proximal and distal hinge support members 56, 55) to align the hinge through holes 52 and slipping the pintle 51 into the aligned through holes. Finally, the pintle 51 is retained within the hinge joint, such as by positioning spring clips on or caps over the ends of the pintle 51.

As a final assembly step, the transducer array assembly 18 and pivot head assembly 50 may be covered by one or more protective coverings which are omitted from FIGS. 11-13 in order to reveal the details of the pivot head assembly 50. Such a protective covering or coverings may be one or more closed end tubular members which may be made from any of the materials described herein for the various sections of the catheter assembly 10. An acoustic window may be provided on the distal end of the protective covering configured from materials that have the appropriately acoustic characteristics to provide a proper acoustic coupling between the transducer array assembly 18 on the inside and body fluids on the outside. A flexible portion of the protective covering may be positioned over the pivot joint part of the pivot head assembly 50. The protective covering may be fused or coupled to the rest of the catheter assembly (e.g., by frictional couplings or adhesives). Once the protective covering is in place over the transducer array assembly 18 and pivot head assembly 50 and fused to the rest of the catheter assembly 10, the distal end of the catheter assembly will be smooth and sealed to prevent intrusion by body fluids.

Figure 14:
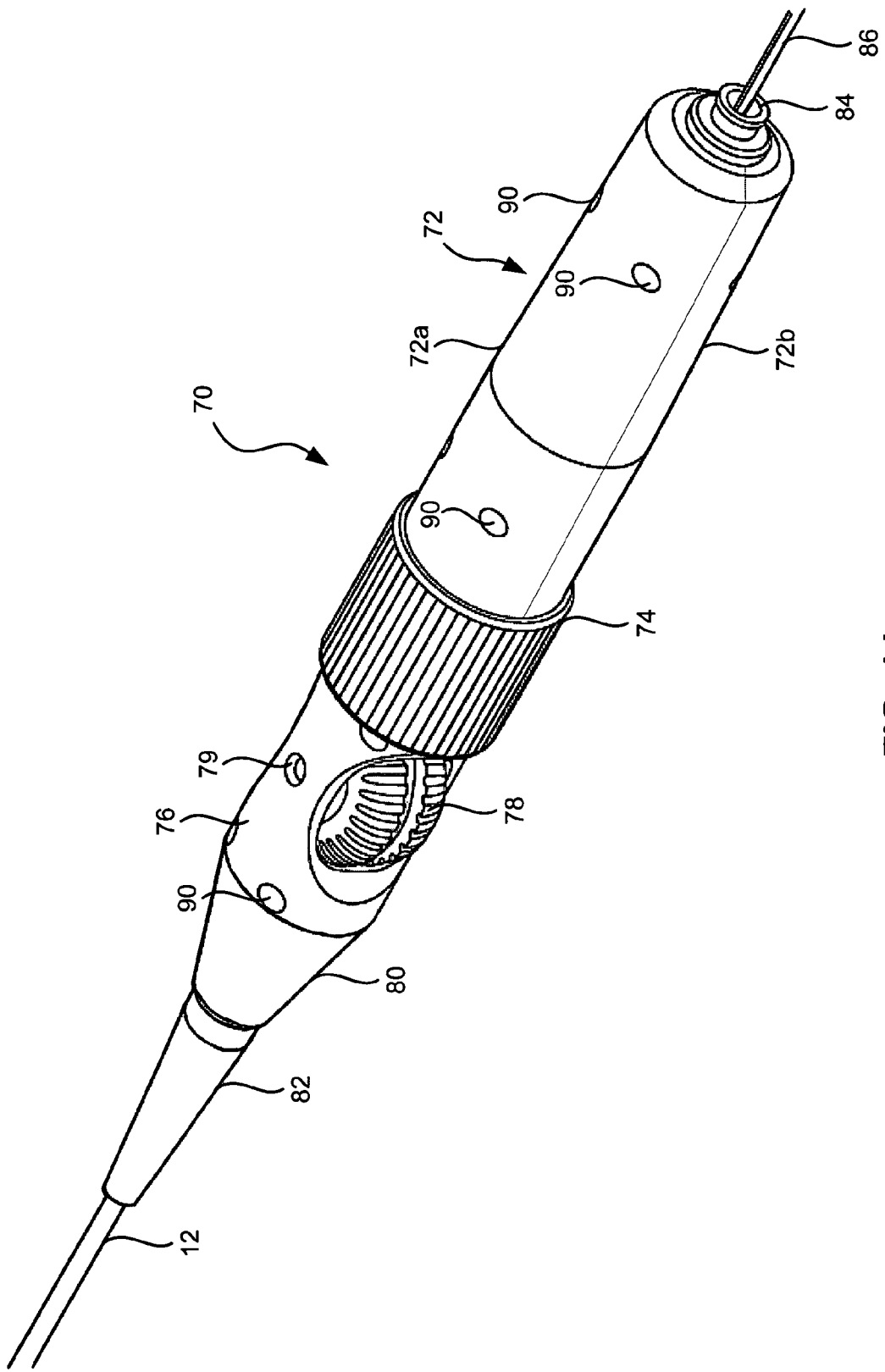
FIG. 14 is a perspective view of a handle portion of the embodiment illustrated in FIG. 3.

At the proximal end of the catheter assembly 10 is a handle assembly 70 providing controls for manipulating the pivot head assembly 50 as well as controlling the bending portion subassembly 48 of steerable catheters. FIG. 14 illustrates an embodiment of the handle assembly 70. In this embodiment, the handle assembly 70 includes a grip portion 72, a steering control manipulator 74 and a pivot control wheel 78. In this embodiment, the steering control manipulator 74 is configured as a rotatable cylinder which is coupled by a screw mechanism to a slide actuator which is shown in more detail in FIGS. 15 and 17. In other embodiments, the steering control manipulator 74 may be in the form of a slide or control wheel positioned within the handle as is known in the art.

The pivot control wheel 78 is configured as two coaxial wheels in this embodiment each rotating about an axle positioned within an axle support hole 79 within a pivot wheel support structure 76. The pivot control wheel 78 is accessible through openings 120 (shown in FIG. 17) on opposing sides of the handle assembly 70. So configured, the pivot control wheel 78 can be actuated by either the left or right hand, allowing left- and right-handed clinicians to manipulate the control wheel with one hand and without having to switch hands.

The handle assembly 70 may also include a transition region cover 80 and a catheter transition piece 82 which together ensure a structural and functional transition from the elongated tubular member 12 to the handle assembly 70. At the proximal end of the handle assembly 70 is a cable support structure 84 through which electrical cables 86 are passed. The electrical cables 86 contain all of the coaxial and other electrical connectors linked to the transducer array assembly 18. The electrical cables 86 extend to a connector (not shown) which is structured to connect to ultrasound imaging equipment, such as an ultrasound imaging system isolation box assembly as described in U.S. patent application Ser. No. 10/998,039 entitled "Safety Systems and Methods for Ensuring Safe Use of Intracardiac Ultrasound Catheters," published as U.S. Patent Application Publication No. 2005/0124899, the entire contents of which are hereby incorporated by reference.

The handle assembly 70 may be configured in pieces to aid fabrication and assembly. For example, the grip portion 72 may be fabricated in upper and lower portions 72a, 72b, which can be fit together and secured using threaded fasteners through faster holes 90. Such construction is illustrated in FIG. 15 which reveals internal structures of the handle assembly 70 with the upper grip portion 72a portion of the handle structure removed.

Figure 15:
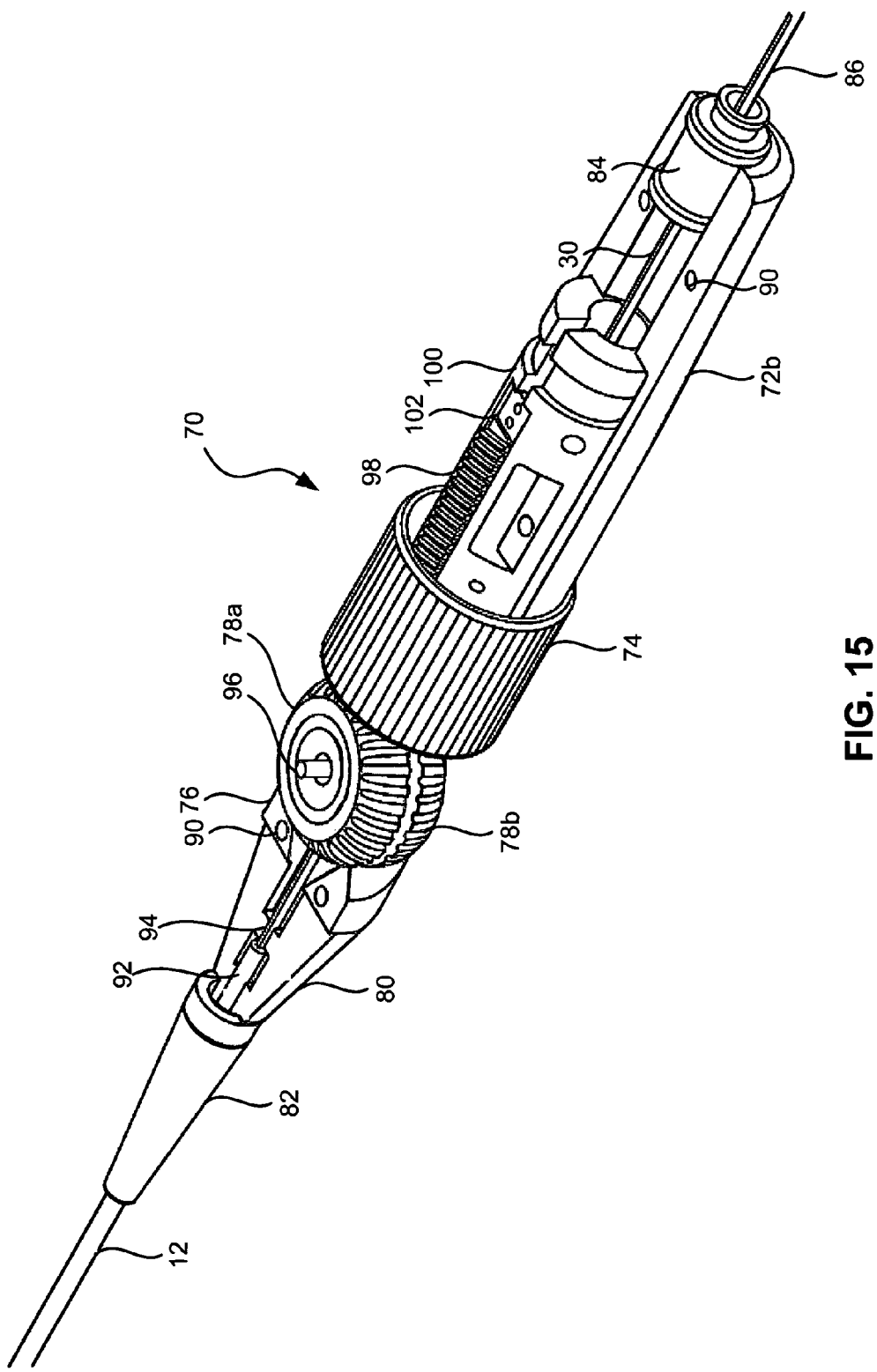
FIGS. 15-17 are cross-sectional views of the handle portion illustrated in FIG. 14.

Referring to FIG. 15, the cable support structure 84 may be configured as a cylinder with ridges configured to fit within corresponding grooves within the upper and lower grip portions 72a, 72b. The cable support structure 84 may include internal structures for transitioning the cable bundle 32 into an external cable having the necessary insulation, RF shielding and protective layers so that the electrical cables 86 complies with requirements for electrical cables used in medical devices. The cable support structure 84 may include internal structures to ensure that tensions and torque applied to the external electrical cables 86 is not transmitted to the relatively fragile internal cable bundle 30.

The cable bundle 30 extends along the centerline of the handle assembly 70 from the cable support structure 84 through to a cable transition portion 94 where the cable bundle 30 is joined with the steering and pivot cables before entering into the proximal end 92 of the elongated tubular member 12.

FIG. 15 reveals how the steering control manipulator 74 interfaces with a slide actuator 98 within a slide slot 102 of an inner support structure 100. In the illustrated embodiment, the steering control manipulator 74 includes internal threads 75 (shown in FIG. 17) which engage the partial threads on the slide actuator 98. When the steering control manipulator 74 is turned in either a clockwise or counterclockwise direction, the internal threads 75 cause the slide actuator 98 to move longitudinally (i.e., proximally or distally) within the slot 102. Longitudinal movement of the slide actuator 98 causes one of the steering cables 42, 44 to be tensioned while the other cable is loosened. As a result, rotational movement of the steering control manipulator 74 can be translated into bending forces applied to the bendable portion subassembly 48 as described above.

FIG. 15 also reveals how the pivot control wheel 78 may be comprised of upper and lower pivot control wheels 78a, 78b each rotating about an axel 96. Rotation of the upper and lower pivot control wheels 78a, 78b drive rotation of a spool 110 (shown in FIG. 16) for controlling the tensioning of pivot cables as shown in more detail in FIG. 16.

On the distal side of the pivot control wheel 78 may be positioned a transition region 94 within the transition region cover 80 in which the various internal parts of the catheter assembly are brought together prior to entering into the elongated tubular member 12. In this region, the cable bundle 30, the steering cables 42, 44 (if present), pivot cables 60 2, 64, and other electrical leads are configured into an arrangement suitable for being threaded into the elongated tubular member 12. At this point, the steering cables 42, 44 may thread into the steering cable conduit 43, and the pivot cables may threaded into the pivot cable conduit 60.

Figure 16:
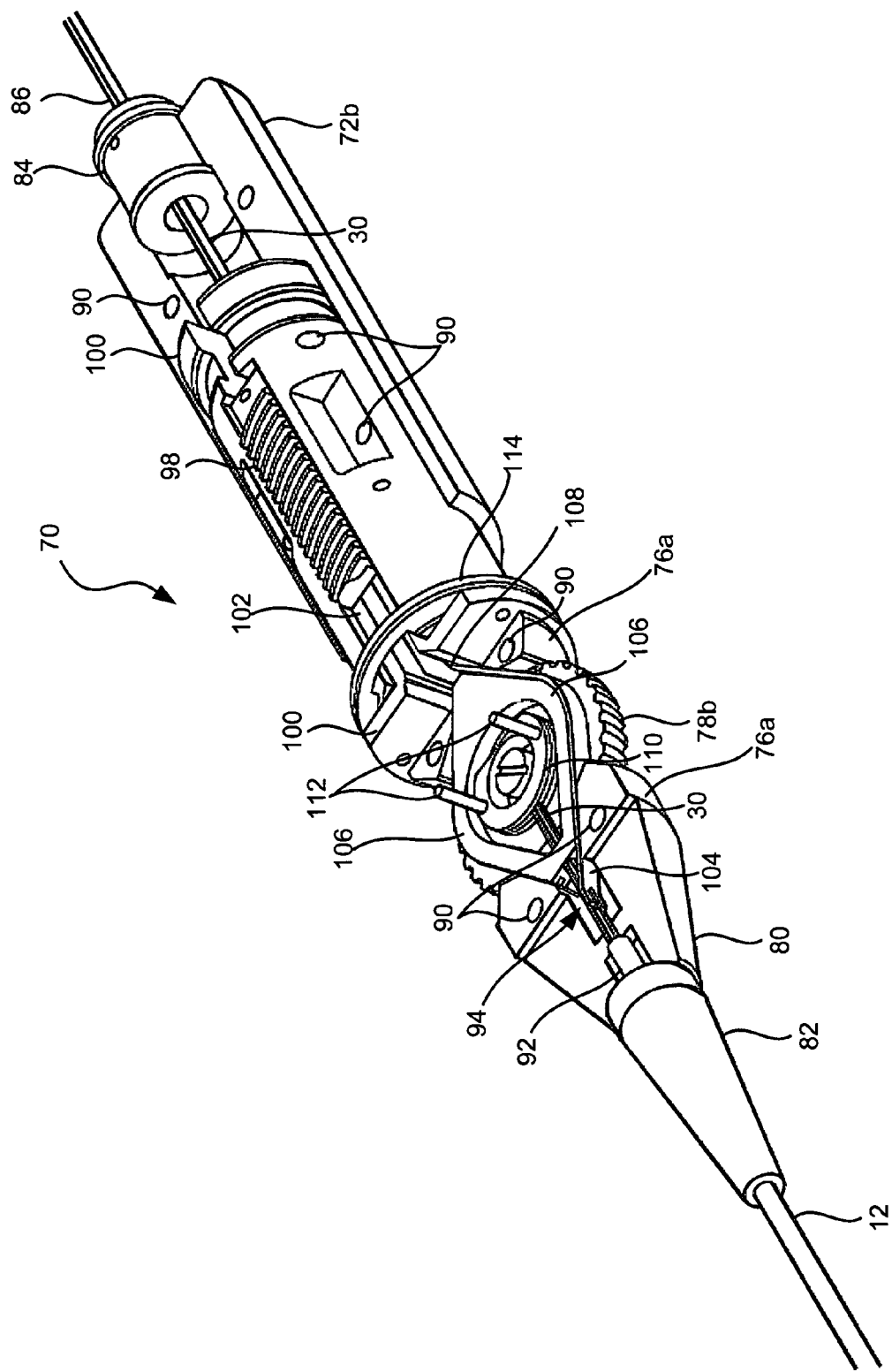

Further details of the handle assembly 70 are revealed in FIG. 16 which shows the assembly with the control manipulator 74 and the upper pivot control wheel 78a removed. As this figure shows, the grip portion 72 may extend over the proximal portion of the handle assembly 70. The internal support structure 100 supporting the slide actuator 98 and associated internal mechanisms for controlling steering cable tension may be configured to extend beyond the grip portion 72, couple to a ring support 114 for the control manipulator 74, and couple to the proximal end of the pivot wheel support structure 76. The ring support 114 provides a bearing support for the control manipulator 74 to permit the manipulator cylinder to be rotated smoothly in either direction. The ring support 114 may be coupled to the internal support structure 100 by threaded connectors, adhesives or other known methods for coupling structures together. The internal support structure may be formed in two halves as illustrated in FIG. 16 to facilitate assembly. The internal support structure 100 also provides a slot 102 for constraining the lateral movement of the slide actuator 98.

FIG. 16 reveals details of the pivot cable tensioning spool 110 which couples to the upper and lower pivot control wheels 78a-78b by dowels 112. The pivot cable tensioning spool 110 may comprise an upper and lower spool between which the cable bundle 30 can pass. One of the pivot cables 62 or 64 is wound about the upper pivot cable tensioning spool 110 in the clockwise direction, while the other pivot cable 62 or 64 is wound about the lower pivot cable tensioning spool 110 in the counterclockwise direction. In this manner, rotation of the pivot control wheels 78 causes one of the pivot cables to be tensioned while the other pivot cable is loosened.

The handle assembly 70 may also include a steering cable bypass guide structure 106 which serves to route the steering cables 42, 44 around the pivot cable tensioning spool 110. This structure may include a guide plate 104 for redirecting the steering cables in line with the cable bundle 30 prior to entering into the proximal end 92 of the elongated tubular member 12. Also, the structure may include a proximal guide 108 to past the steering cables smoothly through the transition provided in the internal support structure 100 before they are connected to the slide actuator 98.

FIG. 16 also reveals how the pivot wheel support structure 76 may be fabricated in two halves which can be coupled together by threaded fasteners through the fastener holes 90. In assembly, the lower pivot control wheel 78b can be lowered into position and rotatably coupled to the lower pivot wheel support structure 76a by an axel 96 which engages an axel support hole 79 (shown in FIG. 14). The axel 96 may include a central shaft having a through hole for accommodating the cable bundle 30. The lower pivot cable tensioning spool 110 can be positioned in the lower pivot control wheel 79b, after which the cable bundle 28 may be threaded through the assembly before the upper pivot cable tensioning spool 110 is positioned in place. At this point, the steering cable bypass guide structure and guide plates may be positioned around the cable tensioning spool 110 and the steering cables routed through the structure to extend into the internal structure 100. Finally, the upper pivot control wheel 78 is installed on the upper pivot cable tensioning spool 110 by sliding over the dowels 112, and the upper pivot wheel support structure (not shown separately). The upper pivot wheel support structure is attached to the lower pivot wheel support structure 76a such as by using threaded fasteners through fastener holes 90. The pivot wheel support structure 76 may then be joined to the internal structure 100, such as by threaded fasteners, locking joints or adhesives.

Figure 17:
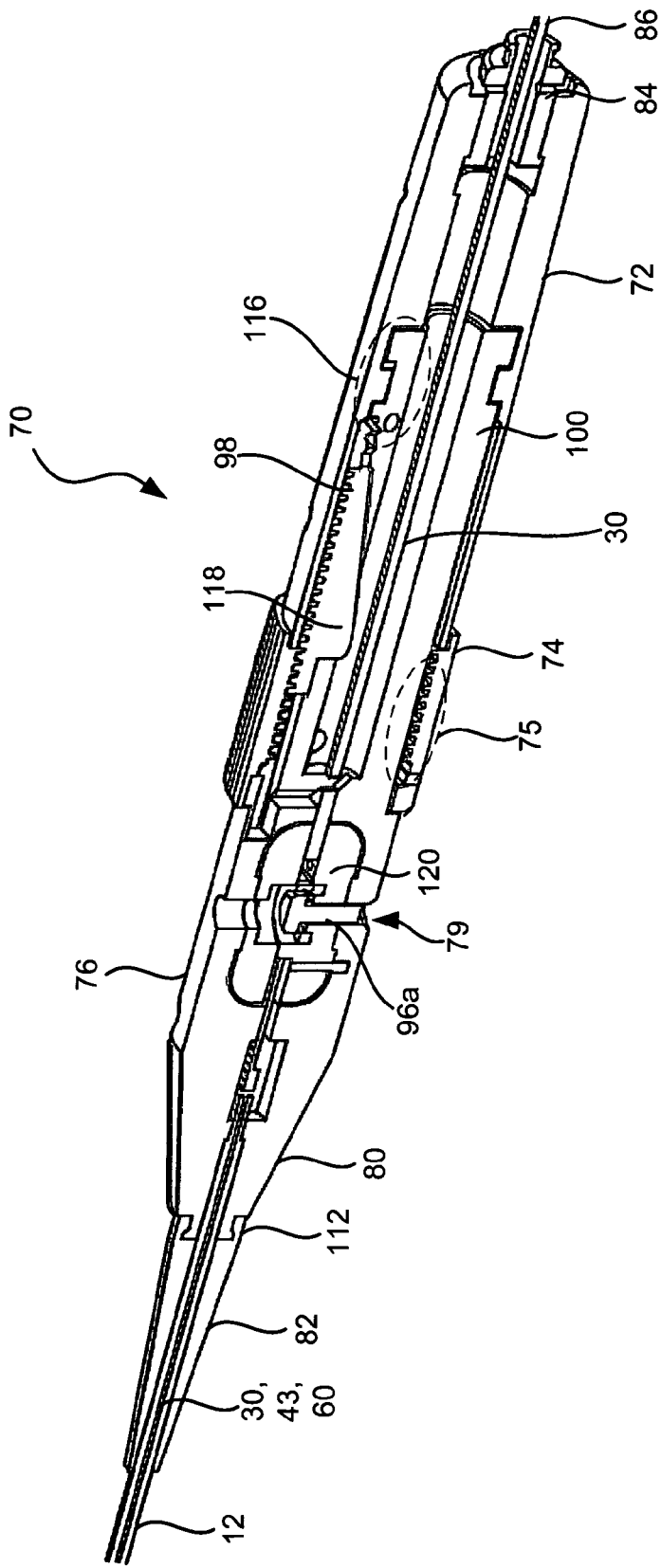

FIG. 17 is a lateral cross-section view of the handle assembly 70 which reveals other internal structure details of illustrated embodiment. For example, as shown in the highlighted region 116, the internal support structure 100 may be configured with tangs and grooves to engage corresponding structures in the grip portion 72 in order to firmly position the two pieces together. The slide actuator 98 may include a portion 118 which extends radially inward between the two halves of the internal support structure 100 in order to engage the steering cables (not shown in FIG. 17). FIG. 17 also reveals the internal threads 75 on the steering control manipulator 74.

FIG. 17 shows how the axel 96 engages the axel support hole 79 within the pivot wheel support structure 76. FIG. 17 shows a two part axel 96 with a lower axel piece 96a shown in place, while the upper axel piece 96 is removed in order show further details about the structure. However, the axel 96 may be provided as a single member which engages both the upper and lower portions of the pivot wheel support structure 76. FIG. 17 also reveals the opening 120 in the pivot wheel support structure 76 for accommodating the pivot control wheels 78.

FIG. 17 also shows a cross-sectional view of the catheter transition piece 82 which may be a tubular member made of flexible material similar to that of the elongated tubular member 12. With a diameter which tapers gradually from the proximal end to the distal end, the catheter transition piece 82 can transition bending stresses so that the elongated tubular member 12 is rigidly supported as it enters the transition region cover 80 without applying a bending force with a sufficiently small radius of curvature to cause the elongated tubular member 12 to kink. A flange and groove attachment configuration 112 may be provided for attaching the catheter transition piece 82 to the transition region cover 80.

Figure 18A:
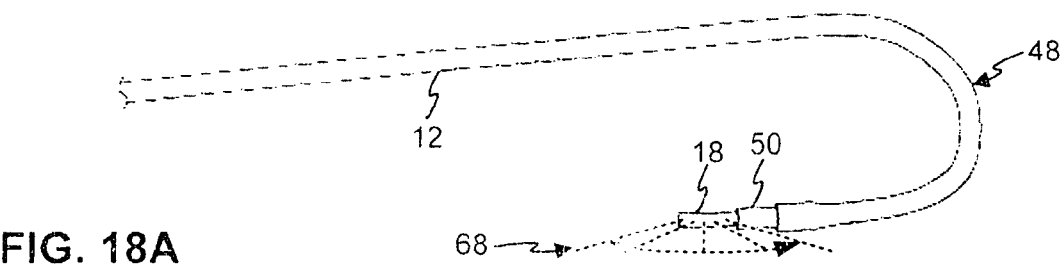
FIGS. 18A-18C are perspective views of the catheter portion of an embodiment illustrating the ultrasound imaging plane at three different angles of rotation.
Figure 18B:
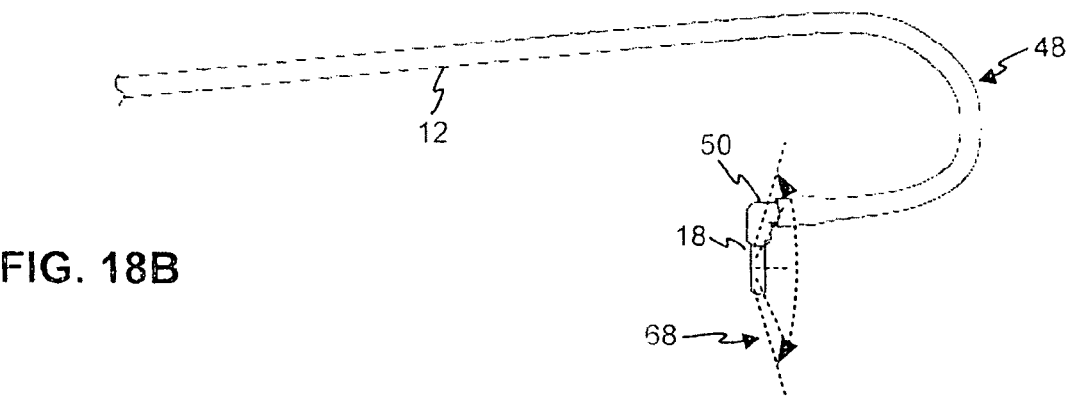
Figure 18C:
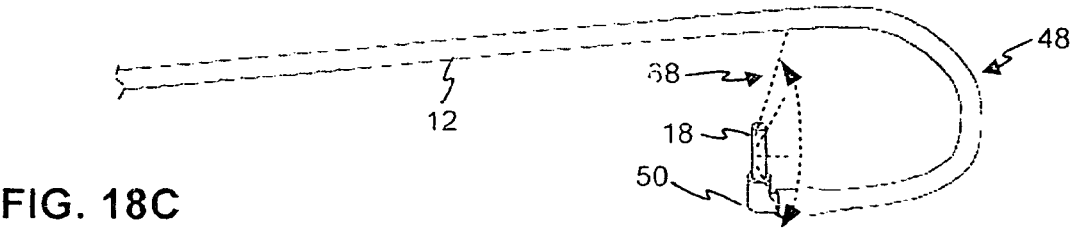

A key operational advantage provided by the various embodiments is illustrated in FIGS. 18A-18C. These figures illustrate the catheter assembly as it may appear when placed within a patient during the conduct of ultrasound imaging. In particular, the bendable portion assembly 48 of the catheter is bent as may be necessary to position the transducer array assembly 18 within a patient's heart. In this configuration, the transducer array assembly 18 can obtain 2-D ultrasound images along the imaging plane 68, which in this illustration is shown as normal to the plane of the paper. Depending upon the examination procedure, a clinician may need to obtain a second 2-D ultrasound image along an orthogonal imaging plane. To do so, the clinician actuates the pivot head assembly 50 (as described more fully above with reference to FIGS. 9-17) to rotate the transducer array assembly 18 through approximately 90° as illustrated in FIG. 18B. As this figure illustrates, the ultrasound imaging planes 68 is now oriented at right angles to the imaging claim illustrated in FIG. 18A. Thus, an orthogonal 2D ultrasound image can be obtained without any movement or other manipulation of the catheter assembly 10 which would fundamentally change the viewing perspective. Thus, the clinician is able to obtain two orthogonal 2D ultrasound images of the same region of interest. In addition to obtaining orthogonal imagery, the clinician may also obtain imagery at any angle between the 0° and 90° deflections illustrated in FIGS. 18A.-18B.

In some positions within the chambers of the patient's heart it may not be possible to deflect the transducer array assembly 18 in the manner illustrated in FIG. 18B due to the presence of nearby heart structure. In such a situation, the clinician may manipulate the pivot head assembly 50 to cause the transducer array assembly 18 to pivot through 90° in the opposite direction as illustrated in FIG. 18C. Again, the ability to deflect the transducer array assembly 18 through 90° between the positions shown in FIGS. 18A and 18C and enables the clinician to obtain orthogonal 2D ultrasound images. Clinicians may also benefit from obtaining a 180° scan of ultrasound images of a structure of interest by incrementally rotating the transducer array assembly from the position illustrated in FIG. 18B to the position illustrated in FIG. 18C.

Figure 19A:
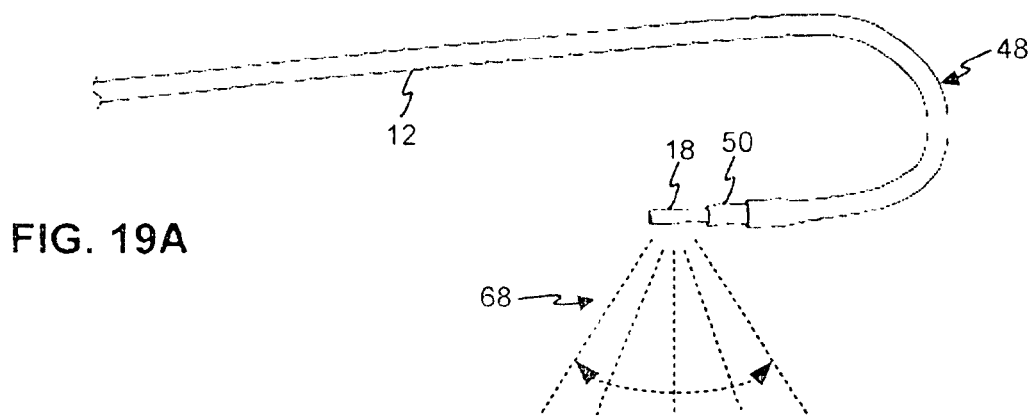
FIGS. 19A-19C are perspective views of the catheter portion of an alternative embodiment illustrating the ultrasound imaging plane at three different angles of rotation.
Figure 19B:
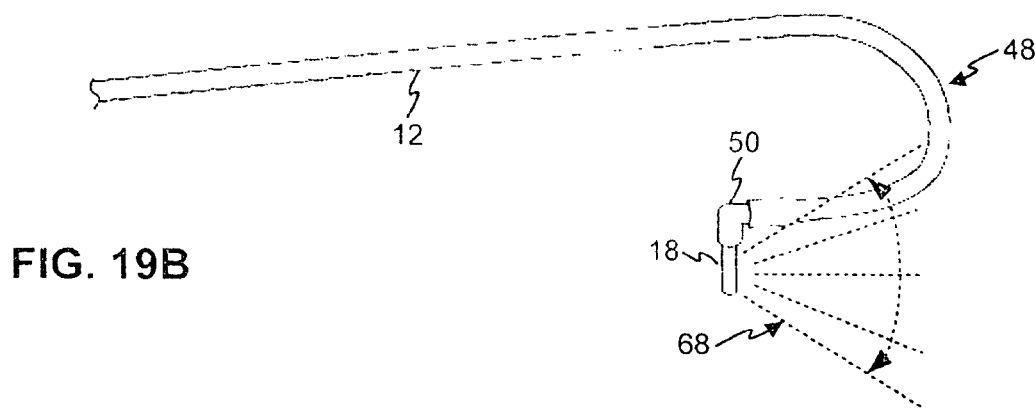
Figure 19C:
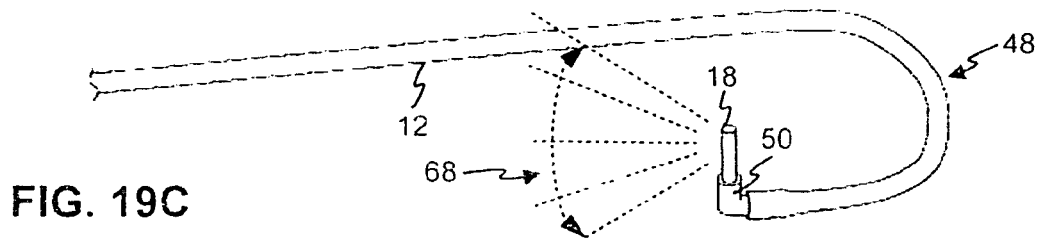

The foregoing embodiments show the transducer array assembly 18 oriented so that the imaging surface is parallel to the plane of rotation provided by the pivot head assembly 50. In this configuration, the imaging plane is orthogonal to the rotational plane, such as illustrated in FIGS. 18A-18C. However, different orientations of the transducer array assembly may be employed in other embodiments. For example, FIGS. 19A-19C show an embodiment in which the transducer array assembly 18 is oriented so that the 2-D ultrasound imaging plane 68 is parallel to the rotation plane of the pivot head assembly 50. In this configuration, the transmission surface of the transducer array assembly 18 is perpendicular to the plane of rotation. In this embodiment, rotation of the pivot head assembly 50 enables the transducer array assembly 18 to provide ultrasound images which pan through 180°. In this manner, the ultrasound transducer array 18 can provide the clinician with ultrasound images of all structures surrounding the pivot head assembly 50 within the imaging plane. Such a catheter assembly 10 may be beneficial in diagnostic procedures where the clinician needs to conduct a survey of the heart and does not have a particular structure of interest at the start of the exam. This embodiment catheter assembly 10 may be used in procedures in combination with the previously described embodiment catheter, with one type of catheter used to conduct a broad survey of the patient's heart and the other catheter used to obtain orthogonal imagery as may be necessary for certain procedures, such as ventricle ejection fraction estimation.

Figure 20:
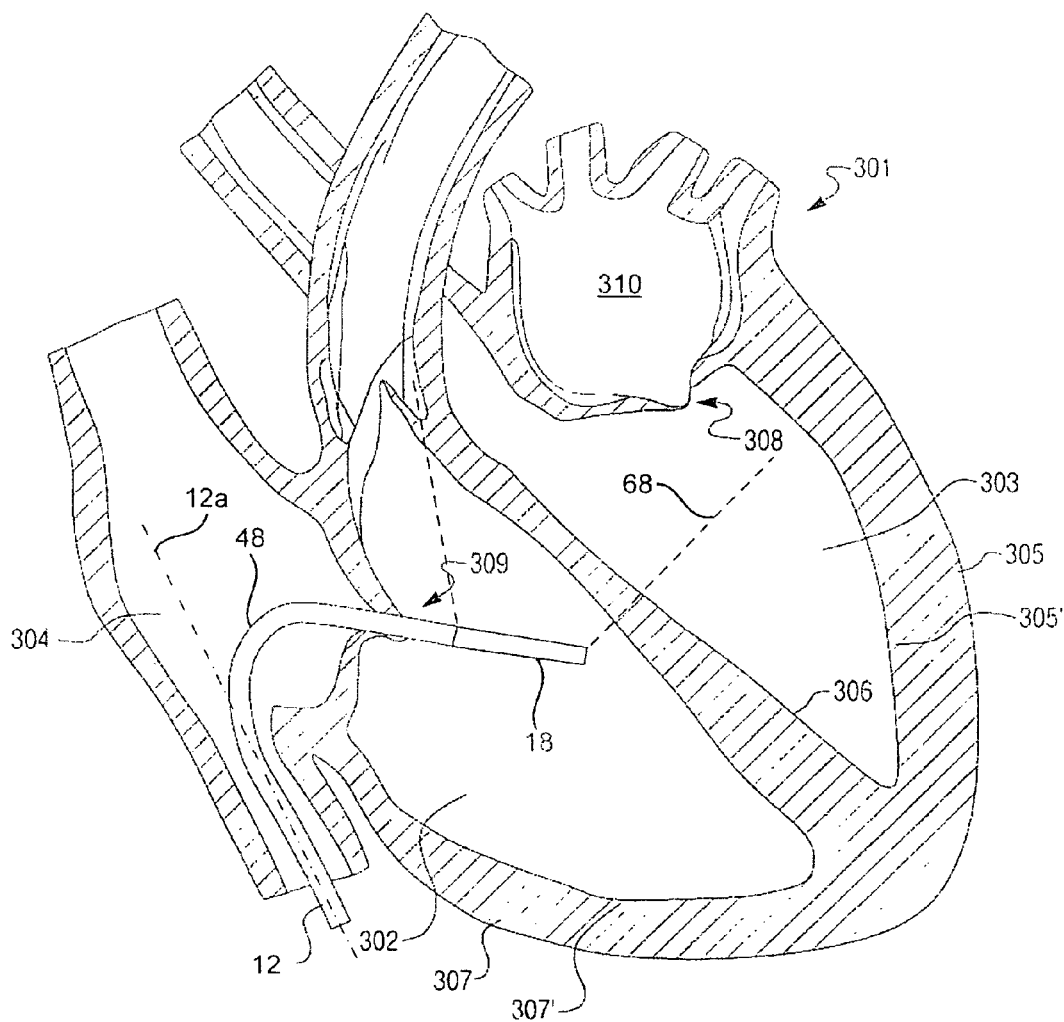
FIGS. 20 and 21 are cross sectional images of a representative heart illustrating an embodiment ultrasound imaging catheter positioned within the right ventricle of a heart by cardiac catheterization via the femoral vein.
Figure 21:
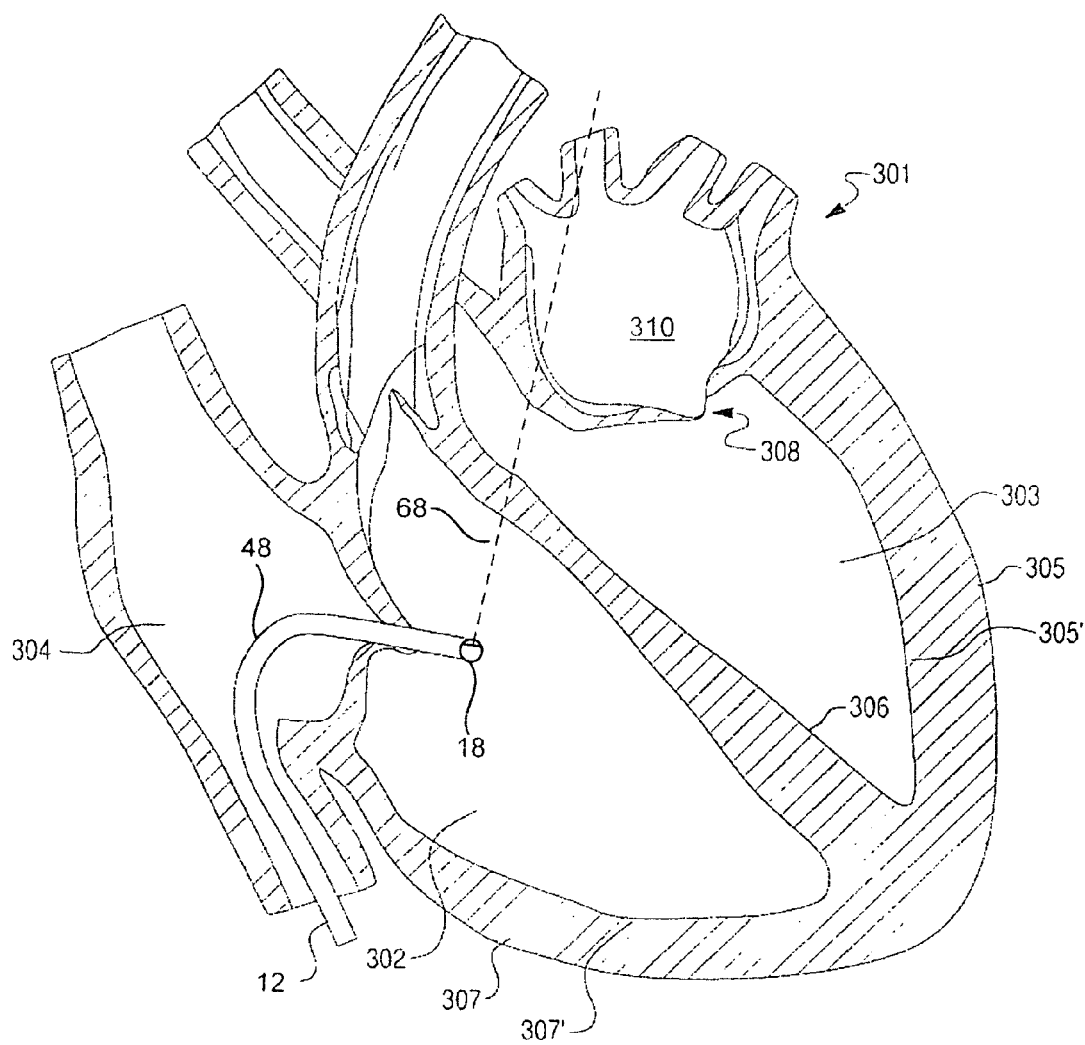

Diagnostic benefits of the various embodiments may be understood with reference to FIGS. 20 and 21 which illustrate the transducer array assembly 18 positioned within the right ventricle 302 of a patient's heart 301. In order to properly place the transducer array assembly 18 into position for imaging the left atrium 310 and bicuspid valve 308, the elongated tubular member 12 can be introduced into the patient's vascular structure via the femoral vein. Using fluoroscopic imaging to monitor the catheter's position, a clinician can advance the distal portion of the catheter into the right atrium 304. In order to guide the catheter through turns in the patient's vascular structure, the clinician may rotate the steering control mechanism 74 in order to introduce a bend into the bendable portion subassembly 48. The clinician may also rotate the entire catheter assembly 10 by rotating the handle assembly 70 in order to orient the bend as necessary to align with the twists and turns in the vascular structure. Once the distal portion of the catheter assembly 10 is in the right atrium 304, the clinician may rotate the steering control mechanism 74 so as to introduce an acute bend in the bendable portion subassembly 48 in order to direct the transducer array assembly 18 through the tricuspid valve 309 and into the right ventricle 302, as shown in FIG. 20. In this position, the field of view of the transducer array assembly 18 (indicated by dotted lines 68) can include portions of the right ventricle 302, the septum 306, the left atrium 310, the bicuspid valve 308, the left ventricle 303, and the left ventricular wall 305. If the transducer array assembly 18 is directed the other way (e.g., if the catheter assembly 10 is turned 180 degrees) the right ventricle 302 and right ventricular wall 307 can be imaged. It is worth noting that if the clinician were to twist the catheter assembly 10 while the catheter is positioned as illustrated in FIG. 20, the transducer array assembly 18 would swing about the long axis 12a of the elongated tubular member 12, which could injure the tricuspid valve 309 or cause the transducer array assembly 18 to strike the right ventricular wall 307 or the septum 306.

To obtain an orthogonal ultrasound image, the clinician can rotate the pivot control wheel 78 in order to cause the transducer array assembly 18 to pivot approximately 90° as illustrated in FIG. 21. In this position, a 2D ultrasound image can be obtained along with the image plane illustrated by the dashed line 68. In this illustration, the 2-D ultrasound image plane is perpendicular to the surface of the paper and extends through an angle which allows imaging of portions of the right ventricle 302, the septum 306, and the left atrium 310.

While FIGS. 20 and 21 illustrate accessing a patient's heart via the femoral vein, access may also be obtained through the jugular or subclavian veins in which case the elongated tubular member 12 would be introduced through the superior vena cava and from the top of the right atrium 304.

While the foregoing embodiments are described in the context of an ultrasound imaging catheter, it should be appreciated that the pivot head assembly and associated structures may also be used in other catheter applications where a zero radius of curvature bend or pivot is required. Thus, the present invention is not necessarily limited to ultrasound imaging catheters, and may be implemented in any catheter that may benefit from having a distal tip capable of pivoting about a hinge.

While the present invention has been disclosed with reference to certain exemplary embodiments, numerous modifications, alterations, and changes to the described embodiments are possible without departing from the sphere and scope of the present invention, as defined in the appended claims. Accordingly, it is intended that the present invention not be limited to the described embodiments, but that it have the full scope defined by the language of the following claims, and equivalents thereof.

I claim:
1. An ultrasound imaging system, comprising:
   a catheter having a proximal end, a distal end, and a bendable portion;
   a pivot assembly coupled to the distal end of the catheter, wherein the pivot assembly comprises a joint;
   an ultrasound imaging transducer assembly coupled to the pivot assembly and extending from the joint and away from the distal end of the catheter; and
   a handle assembly coupled to the proximal end of the catheter, the handle assembly comprising:
      a pivot control actuator coupled to the pivot assembly and configured so that movement of the pivot control actuator causes the ultrasound imaging transducer assembly to pivot about the joint; and
      a steering control actuator coupled to the bendable portion of the catheter and configured so that actuation of the steering control actuator causes the bendable portion of the catheter to bend.

2. The ultrasound imaging system as in claim 1, wherein rotational movement of the pivot assembly has a zero radius of curvature.

3. The ultrasound imaging system as in claim 1, wherein the pivot assembly comprises:
   a proximal support structure coupled to the catheter;
   a distal support structure coupled to the ultrasound imaging transducer assembly; and a pintle having a long axis, wherein the proximal and distal support structures are rotatably coupled by the pintle to form the joint, wherein the joint is a hinge joint.

4. The ultrasound imaging system of claim 3, wherein the ultrasound imaging transducer assembly is oriented with respect to the hinge joint so that an imaging plane is perpendicular to the long axis of the pintle.

5. The ultrasound imaging system of claim 3, wherein the ultrasound imaging transducer assembly is oriented with respect to the hinge joint so that an imaging plane is parallel to the long axis of the pintle.

6. The ultrasound imaging system of claim 3, further comprising:
a first pivot control cable coupled to the distal support structure and threaded through the catheter to the proximal end of the catheter; and
a second pivot control cable coupled to the distal support structure and threaded through the catheter to the proximal end of the catheter.

7. The ultrasound imaging system of claim 6, wherein the pivot control actuator is coupled to the first and second pivot control cables and configured so that movement of the pivot control actuator tensions one of the first and second pivot control cables sufficient to cause the ultrasound imaging transducer assembly to pivot about the hinge joint.

8. The ultrasound imaging system of claim 7, wherein the pivot control actuator comprises:
a pivot wheel support structure;
an axel positioned within the pivot wheel support structure;
a pivot wheel rotatably coupled to the pivot wheel support structure via the axel; and
a spool coupled to the pivot wheel and to the a first and second pivot control cables, wherein the first and second pivot control cables are coupled to the spool so that rotation of the pivot wheel in a first direction causes the first pivot control cable to be tensioned while the second pivot control cable is loosened and rotation of the pivot wheel in a second direction opposite the first direction causes the second pivot control cable to be tensioned while the first pivot control cable is loosened.

9. The ultrasound imaging system of claim 7, further comprising:
a bendable portion subassembly coupled between the pivot assembly and the distal end of the catheter;
first and second steering cables coupled to the bendable portion subassembly; and
a steering control actuator coupled to the handle assembly and the first and second steering cables,
wherein the steering control actuator, first and second steering cables and bendable portion subassembly are configured so that actuation of the steering control actuator in a first actuator direction causes the bendable portion subassembly to bend in a first bending direction and actuation of the steering control actuator in a second actuator direction opposite the first actuator direction causes the bendable portion subassembly to bend in a second bending direction.

10. The ultrasound imaging system of claim 9, wherein the ultrasound imaging transducer assembly is oriented with respect to the catheter so that an imaging plane is orthogonal to a plane defined by a bend in the bendable portion subassembly.

11. The ultrasound imaging system of claim 9, wherein the steering control actuator comprises:
a cylinder encircling and rotatably coupled to the handle assembly, the cylinder having threads on an interior surface; and
a slide actuator slidably coupled to the handle assembly and to the first and second steering cables, the slide actuator having partial threads on an outer surface configured to engage the threads on the interior surface of the cylinder, wherein:
the handle assembly includes a slot configure to constrain motion of the slide actuator parallel to a long axis of the handle assembly;
the slide actuator is coupled to the first and second steering cables so that when the slide actuator moves in a proximal direction the first steering cable is tensioned while the second steering cable is loosened and when the slide actuator moves in a distal direction the second steering cable is tensioned while the first steering cable is loosened.

12. An ultrasound imaging catheter, comprising:
an elongate member having a proximal end, a distal end, and a bendable portion;
a pivot assembly coupled to the distal end of the elongate member, wherein the pivot assembly comprises a joint;
an ultrasound imaging transducer assembly coupled to the pivot assembly and extending from the joint and away from the distal end of the elongate member; and
a handle assembly coupled to the proximal end of the elongate member, the handle assembly comprising:
means for pivoting the ultrasound imaging transducer through an angle in response to user pivot control actuations; and
means for bending the elongate member in response to user steering control actuations.

13. The ultrasound imaging catheter of claim 12, wherein the means for pivoting the ultrasound imaging transducer through an angle in response to user pivot control actuations comprises:
first and second pivot control cables;
means for pivoting the ultrasound imaging transducer in response to tension applied to one of the first and second pivot control cables; and
means for tensioning one of the first and second pivot control cables in response to user actuation.

14. The ultrasound imaging elongate member of claim 12, wherein the means for bending the elongate member in response to user steering control actuations comprises:
first and second steering control cables;
means for bending the elongate member in response to tension applied to one of the first and second steering control cables; and
means for tensioning one of the first and second steering control cables in response to user actuation.

15. A catheter assembly, comprising:
an elongate member comprising a proximal portion and a distal portion;
an ultrasound transducer pivotably coupled to the distal portion of the elongate member and extending therefrom; and
a handle coupled to the proximal portion of the elongate member, the handle comprising:
a grip portion;
a pivot control actuator movably coupled to the grip portion and operably coupled to the ultrasound transducer such that movement of the pivot control actuator relative to the grip portion causes the ultrasound transducer to rotate with respect to the distal portion of the elongate member; and
a steering control actuator movably coupled to the grip portion and operably coupled to the distal portion of the catheter such that movement of the steering control actuator relative to the grip portion causes the distal portion of the elongate member to bendably deflect.

16. The catheter assembly of claim 15, further comprising:
first and second pivot control cables;
means for rotating the ultrasound imaging transducer in response to tension applied to one of the first and second pivot control cables; and
means for tensioning one of the first and second pivot control cables in response to user actuation of the pivot control actuator.

17. The catheter assembly of claim 15, further comprising:
first and second steering control cables;
means for bendably deflecting the elongate member in response to tension applied to one of the first and second steering control cables; and
means for tensioning one of the first and second steering control cables in response to user actuation of the steering control actuator.

18. The catheter assembly of claim 15, wherein the ultrasound transducer is oriented with respect to the elongate member such that an imaging plane is orthogonal to a plane defined by a bend in the distal portion of the elongate member when the elongate member is bendably deflected to create the bend and the ultrasound transducer is rotated from an initial position to a rotated position.

19. The catheter assembly of claim 15, wherein the ultrasound transducer is rotatably coupled to the distal portion of the elongate member by a pivot assembly, the pivot assembly comprising:
a proximal support structure coupled to the elongate member;
a distal support structure coupled to the ultrasound transducer; and
a pintle having a long axis, wherein the proximal and distal support structures are rotatably coupled by the pintle to form a hinge joint.

20. The catheter assembly of claim 19, further comprising:
a first pivot control cable coupled to the distal support structure and threaded through the elongate member to the proximal portion; and
a second pivot control cable coupled to the distal support structure and threaded through the elongate member to the proximal portion;
wherein the pivot control actuator is operably coupled to the first and second pivot control cables such that movement of the pivot control actuator tensions one of the first and second pivot control cables sufficient to cause the ultrasound transducer to rotate about the hinge joint.

* * * * *